United States Patent
Sancoff et al.

(10) Patent No.: US 6,383,208 B1
(45) Date of Patent: May 7, 2002

(54) APPARATUS AND METHOD FOR APPROXIMATING AND CLOSING THE WALLS OF A HOLE OR PUNCTURE IN A PHYSIOLOGICAL SHELL STRUCTURE

(75) Inventors: Gregory E. Sancoff; Frederic P. Field, both of North Hampton, NH (US)

(73) Assignee: Onux Medical, Inc., Hampton, NH (US)

( * ) Notice: Subject to any disclaimer, the term of this patent is extended or adjusted under 35 U.S.C. 154(b) by 0 days.

(21) Appl. No.: 09/706,471

(22) Filed: Nov. 3, 2000

Related U.S. Application Data

(60) Provisional application No. 60/163,923, filed on Nov. 5, 1999.

(51) Int. Cl.[7] .............................................. A61B 17/04
(52) U.S. Cl. ...................................... 606/213; 606/144
(58) Field of Search ................................ 606/213, 139, 606/144, 148

(56) References Cited

U.S. PATENT DOCUMENTS

| | | | | |
|---|---|---|---|---|
| 5,431,639 A | * | 7/1995 | Shaw ........................... | 606/213 |
| 5,728,114 A | * | 3/1998 | Evans et al. ................. | 606/213 |
| 5,810,884 A | * | 9/1998 | Kim ............................. | 606/213 |
| 5,817,110 A | * | 10/1998 | Kronner ...................... | 606/213 |
| 5,830,232 A | * | 11/1998 | Hasson ........................ | 606/213 |
| 6,024,755 A | * | 2/2000 | Addis .......................... | 606/213 |
| 6,056,768 A | * | 5/2000 | Cates .......................... | 606/213 |
| 6,059,816 A | * | 5/2000 | Moenning .................... | 606/213 |
| 6,152,948 A | * | 11/2000 | Addis .......................... | 606/213 |
| 6,206,893 B1 | * | 3/2001 | Klein et al. .................. | 606/213 |
| 6,248,124 B1 | * | 6/2001 | Pedros et al. ................ | 606/213 |
| 6,287,322 B1 | * | 9/2001 | Zhu et al. .................... | 606/213 |

* cited by examiner

*Primary Examiner*—Gary Jackson
(74) *Attorney, Agent, or Firm*—Pandiscio & Pandiscio

(57) ABSTRACT

Apparatus for approximating and closing the walls of a hole or puncture in a physiological shell structure which, in one preferred form, comprises a pair of components that manipulate wire suture. The first component, sometimes referred to herein as a suture introducer, locates the edges of the hole and passes wire suture through them. The second component, sometimes referred to herein as a suture tensioner, gathers the free ends of the wire suture and twists them together, which in turn closes the hole. After the wire suture has been twisted sufficiently to effect closure, the excess wire is trimmed away. The apparatus can deploy more than one wire suture at a time if desired. Using self-locating features and tactile feedback, the apparatus is particularly well adapted to access remote surgical sites.

7 Claims, 27 Drawing Sheets

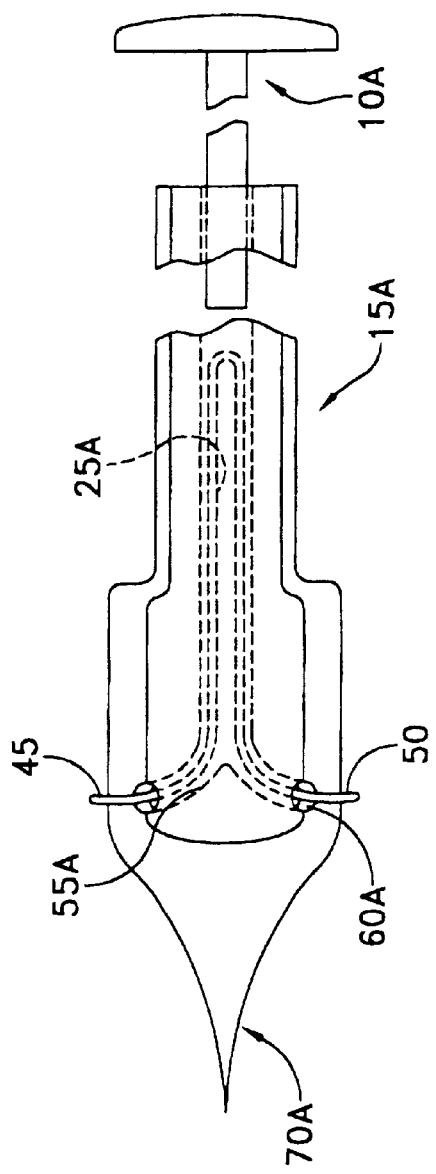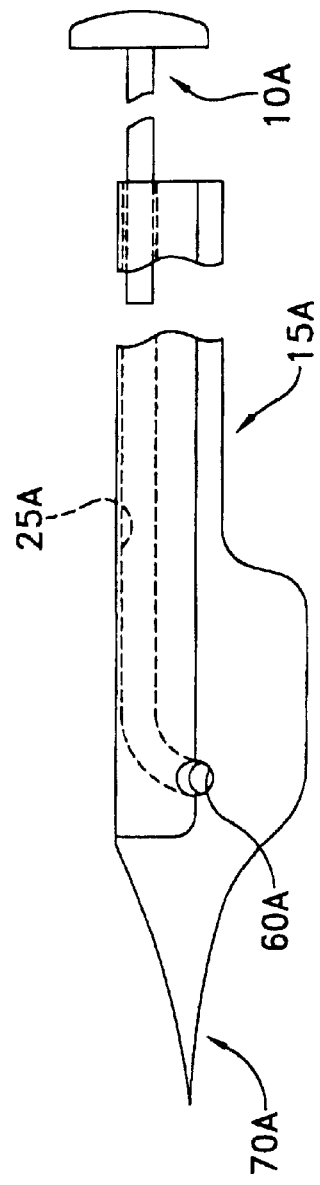

APPARATUS AND METHOD FOR APPROXIMATING AND CLOSING THE WALLS OF A HOLE OR PUNCTURE IN A PHYSIOLOGICAL SHELL STRUCTURE

REFERENCE TO PENDING PRIOR PATENT APPLICATION

This patent application claims benefit of pending prior U.S. Provisional Patent Application Ser. No. 60/163,923, filed Nov. 5, 1999 by Gregory E. Sancoff et al. for DEVICE FOR APPROXIMATING AND CLOSING THE WALLS OF A HOLE OR PUNCTURE IN A PHYSIOLOGICAL SHELL STRUCTURE, which pending prior patent application is hereby incorporated herein by reference.

FIELD OF THE INVENTION

This invention relates to surgical apparatus and methods in general, and more particularly to apparatus and methods for approximating and closing the walls of a hole or puncture in a physiological shell structure.

BACKGROUND OF THE INVENTION

Many surgical procedures require the insertion of instruments or catheters into vessels or organs through a small insertion placed in the wall of the structure (e.g., arteries and veins). Once the procedure is completed, these holes often need to be closed with sutures. Unfortunately, when the hole is difficult to see or physically reach, conventional needles and sutures are not easily utilized since this requires finding the edges of the hole, passing sutures through the edges, and then tying secure knots.

As a result, one object of the present invention is to provide means for locating and suturing remote tissue edges.

Another object of the present invention is to provide for the delivery of a device to the surgical site that locates itself to the tissue edges so that the device can deliver needleless sutures (e.g., needleless wire sutures) for tissue closure.

And another object of the present invention is to provide for needleless suturing of tissue so as to eliminate the need to shuttle a needle in and out of the tissue where there is little room to do so.

Still another object of the present invention is to provide means for producing a knot (e.g., twists or turns) in the wire suture that does not require the cumbersome manual manipulations of the surgeon.

Yet another object of the present invention is to provide suturing means whereby both the suture placement and the knot formation are somewhat automated, yet the surgeon still has tactile feedback in these operations so that control is not lost.

And another object of the present invention is to provide a novel method for approximating tissue.

SUMMARY OF THE INVENTION

These and other objects are addressed by the present invention which, in one preferred form, comprises a pair of components that manipulate wire suture so as to close holes in physiological shell structures. The first component, sometimes hereinafter referred to as a suture introducer, locates the edges of the holes and passes wire suture through them. The second component, sometimes hereinafter referred to as a suture tensioner, gathers the free ends of the wire suture and twists them together, which in turn closes the holes. After the wire suture has been twisted sufficiently to effect closure, the excess wire is trimmed away. The apparatus can deploy more than one wire suture at a time if desired. Using self-locating features and tactile feedback, the apparatus is particularly well adapted to access remote surgical sites.

BRIEF DESCRIPTION OF THE DRAWINGS

These and other objects and features of the present invention will be more fully disclosed or rendered obvious by the following detailed description of the preferred embodiments, which is to be considered together with the accompanying drawings wherein like numbers refer to like parts and further wherein:

FIGS. 27 and 28 show front and side views of selected portions of the suture introducer shown in FIG. 26.

DETAILED DESCRIPTION OF THE PREFERRED EMBODIMENTS

The present invention uses two components to place wire sutures. The first component, sometimes hereinafter called the suture introducer, locates the tissue edges which are to be approximated and deploys the suture wire through the edges of the tissue at approximately opposite sides of the opening. The suture introducer is then removed and the second component, sometimes hereinafter called the suture tensioner, is introduced in order to gather the two free ends of the suture wire together and allow the user to twist those ends together until the opposing edges of the tissue are brought in close approximation to each other. The suture tensioner then allows the user to cut off and remove the excess wire.

Figure 1:
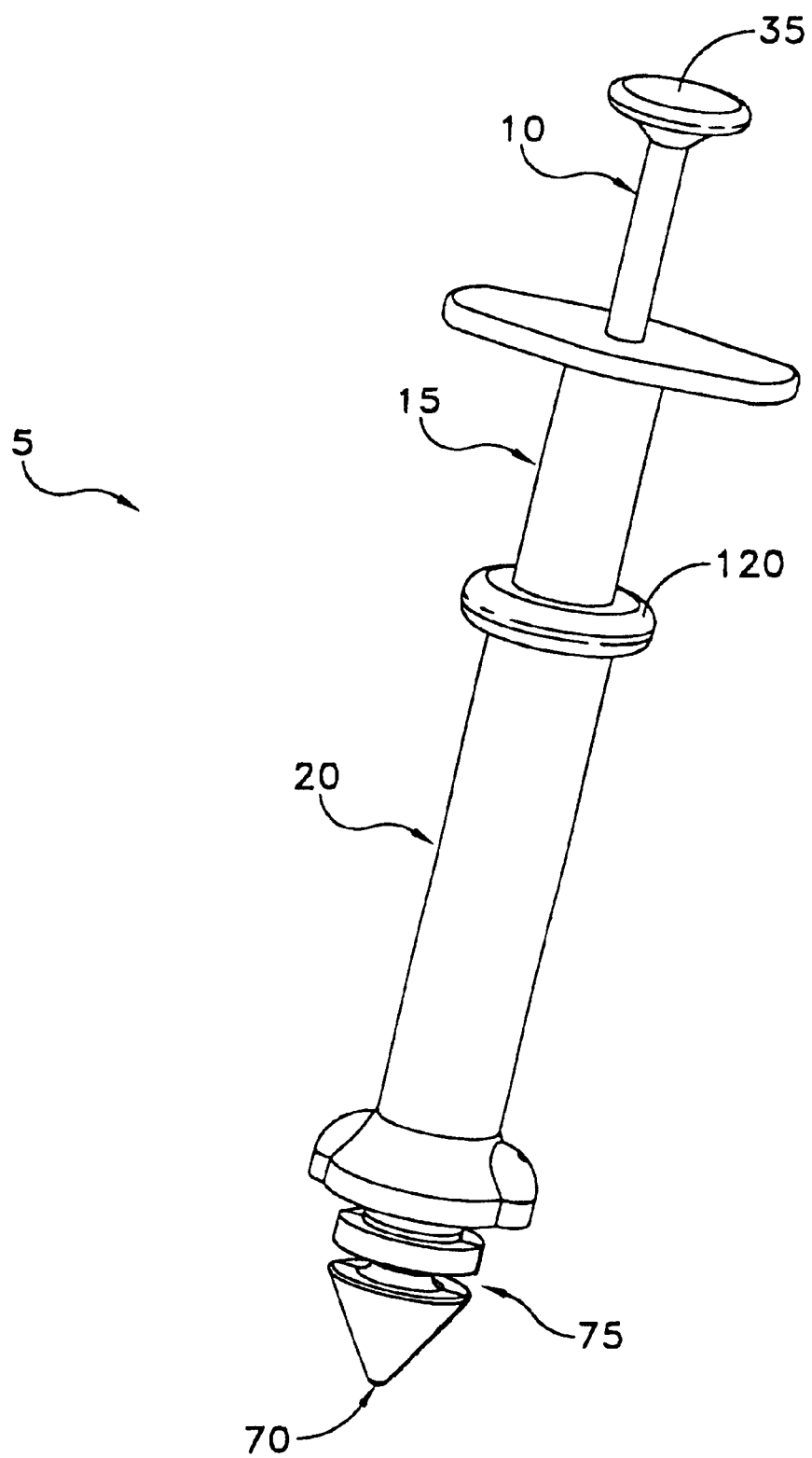
FIGS. 1 and 2 are perspective views of a suture introducer formed in accordance with the present invention.
Figure 2:
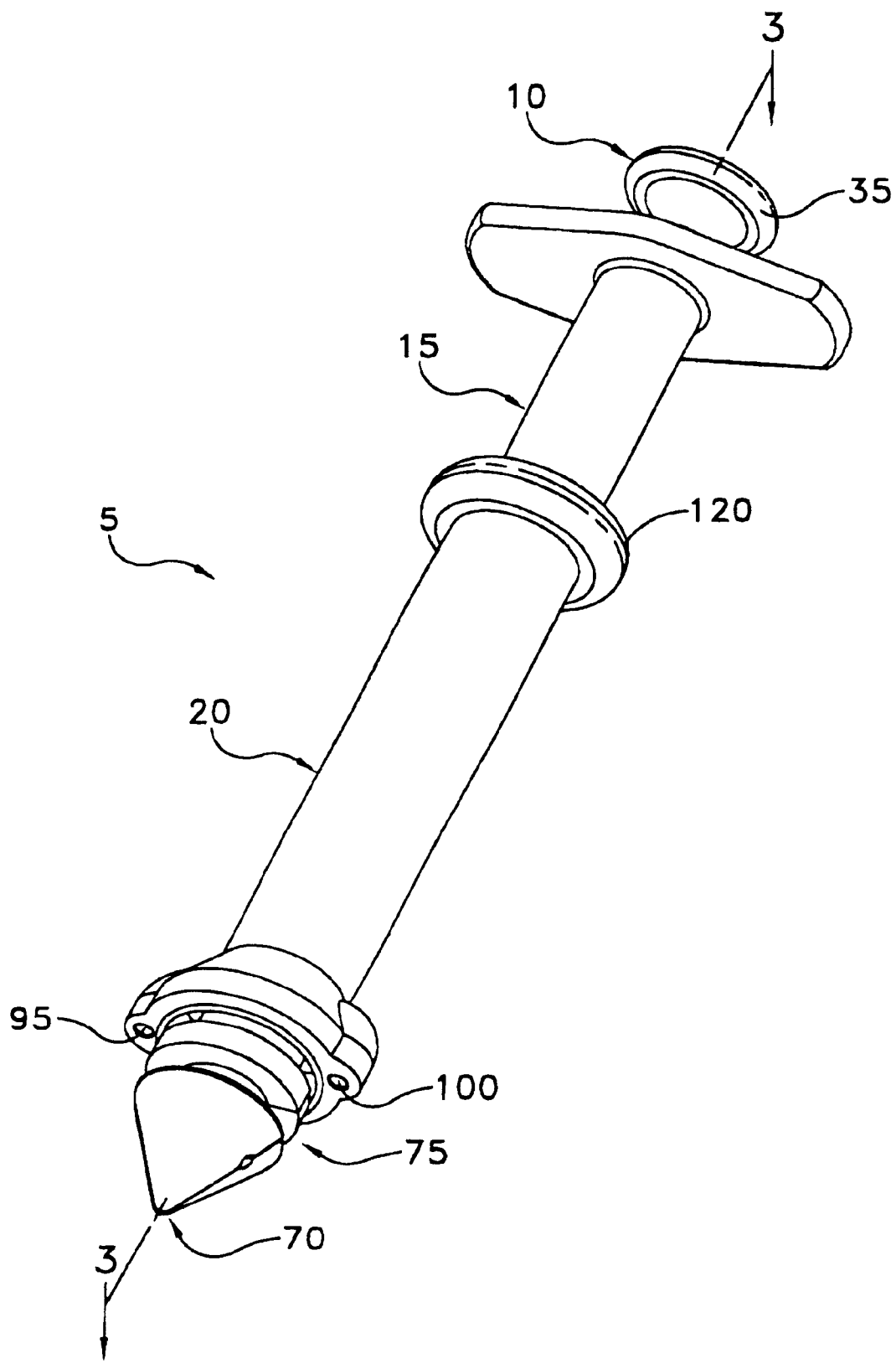
Figure 3:
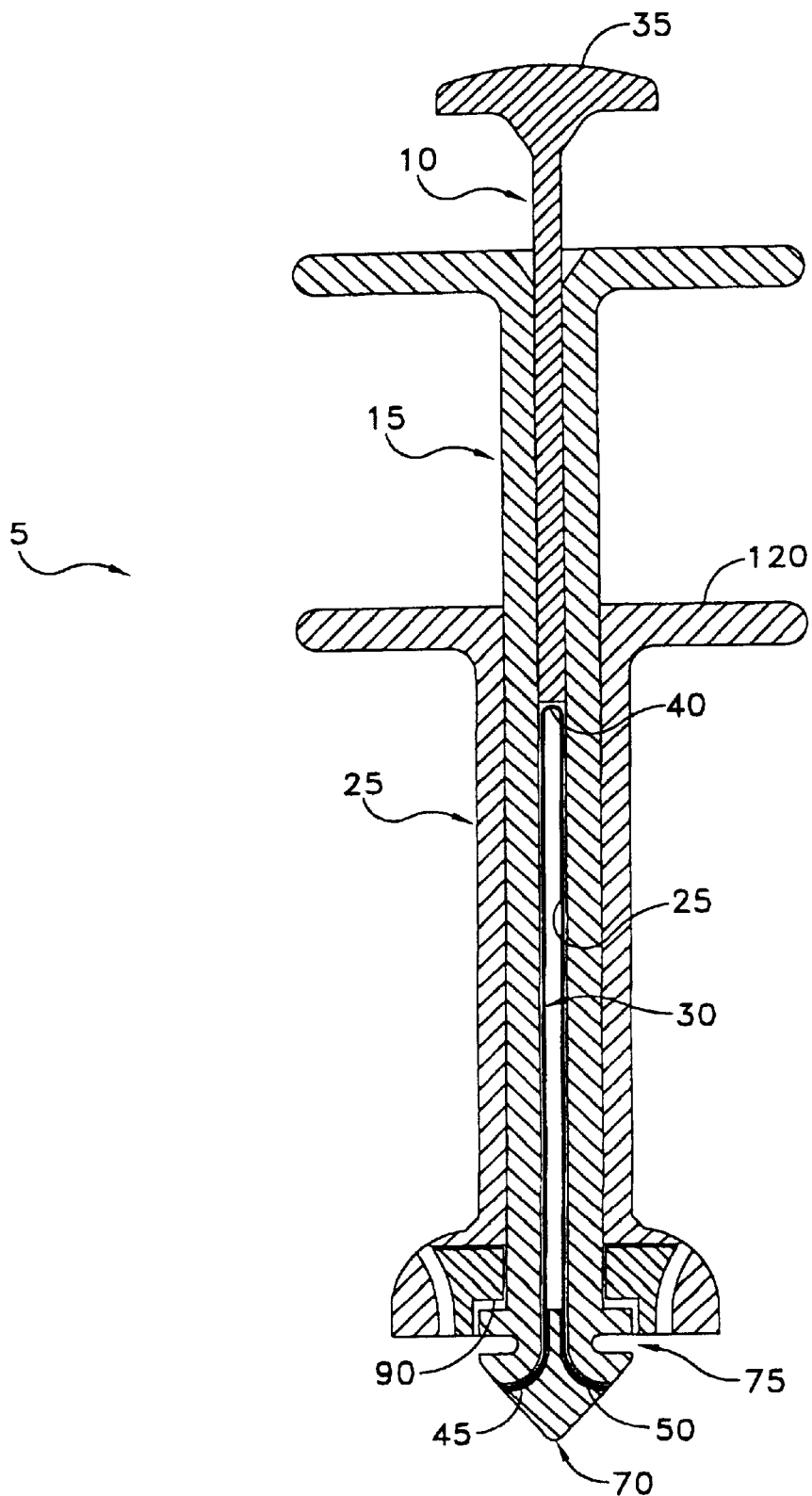
FIG. 3 is a cross-sectional view of the suture introducer shown in FIGS. 1 and 2.

Looking now at FIGS. 1–13, there is shown a suture introducer 5 formed in accordance with the present invention. Suture introducer 5 generally comprises three concentric elements: a wire advance plunger 10, a housing 15, and a sleeve 20. As seen in FIG. 3, wire advance plunger 10 is the innermost element and is located on the inside of housing 15 at the housing's proximal end. Sleeve 20 is located on the outside of housing 15 at the housing's distal end.

Housing 15 has an inner channel 25 (see FIGS. 3–5) that contains the suture wire 30. Wire advance plunger 10 is located inside the proximal end of wire channel 25. The proximal end of plunger 10 comprises a round knob 35 against which the user can manually apply pressure so as to initiate wire deployment. The distal end of wire advance plunger 10 is located proximally to the proximal end of suture wire 30. Advancing plunger 10 causes the plunger to push suture wire 30 distally down channel 25.

The cross-sectional shape of channel 25 (see FIG. 5) is generally rectangular with rounded corners so that the channel can snugly hold two strands of suture wire 30 that are arranged alongside each other. The cross-sectional shape of plunger 10 conforms to the cross-sectional shape of channel 25 for a distance at least equal to the stroke length of the plunger. The two strands of suture wire 30 are part of the same piece of wire which has been folded at a midpoint 40 (see FIG. 3). The wire midpoint 40 is located near the distal end of the plunger (see FIG. 3) and the two free ends 45, 50 (see FIGS. 3, 4 and 9) of the wire are located near the distal end of the housing.

Figure 11:
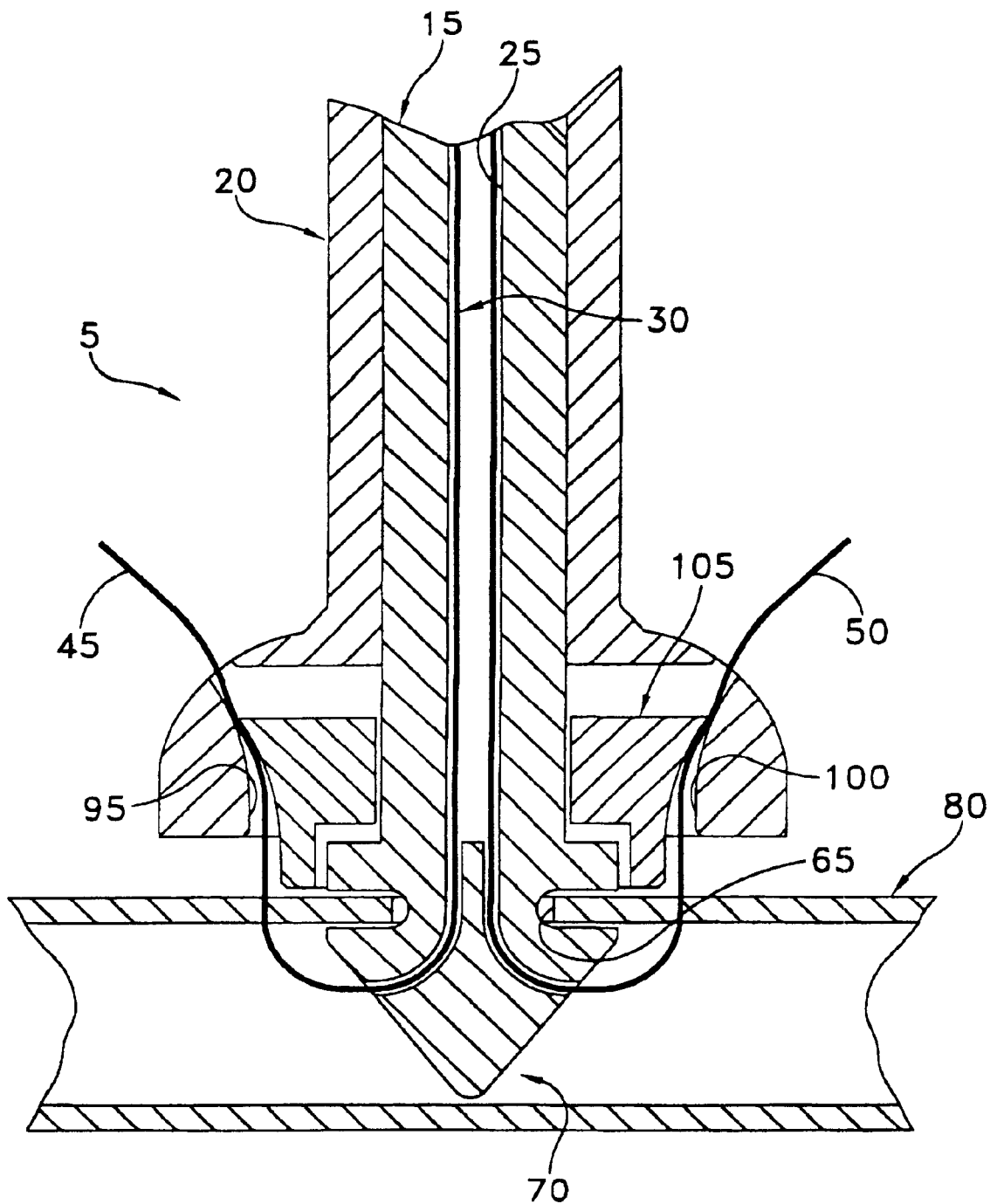
Figure 12:
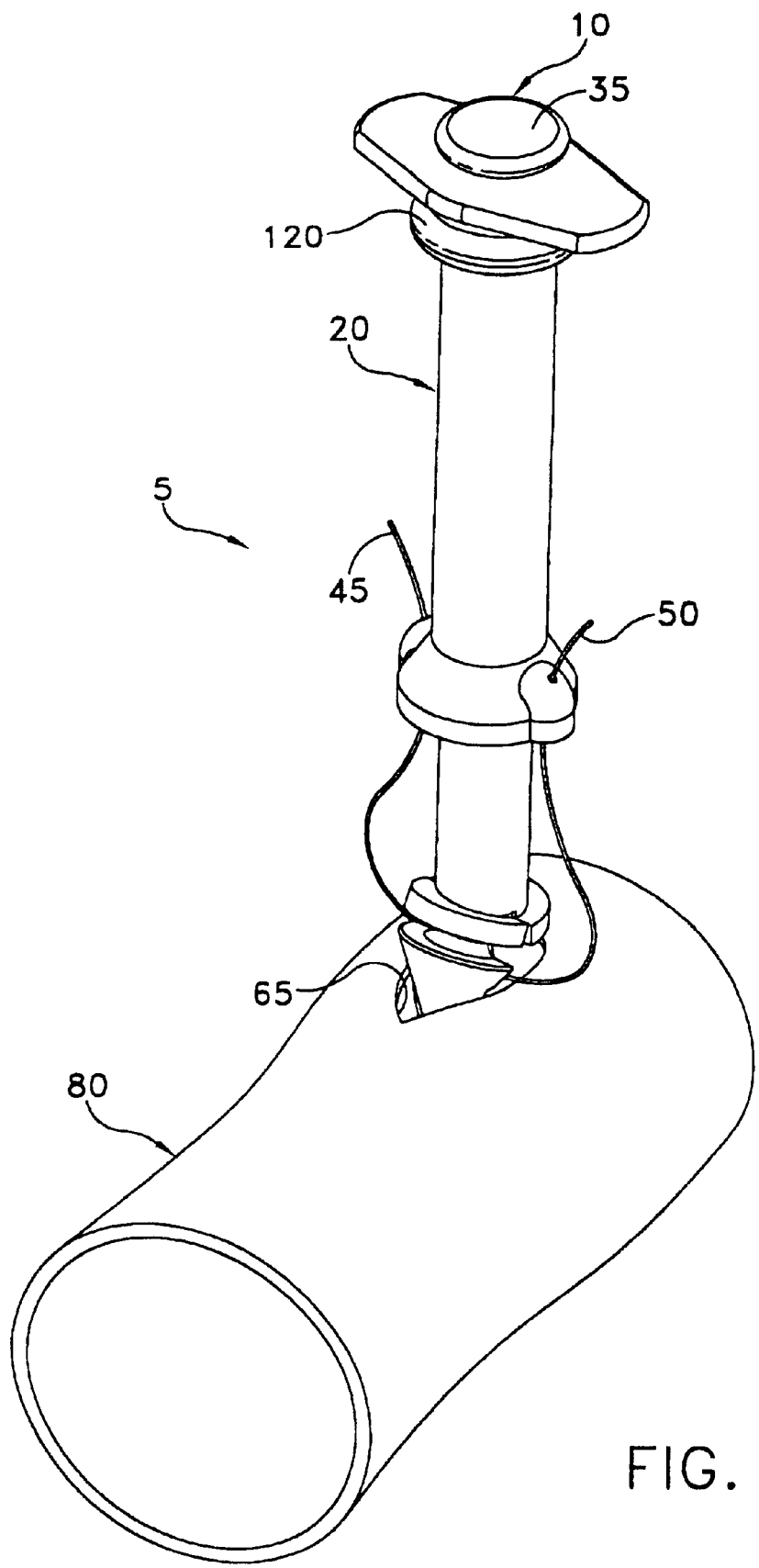
Figure 13:
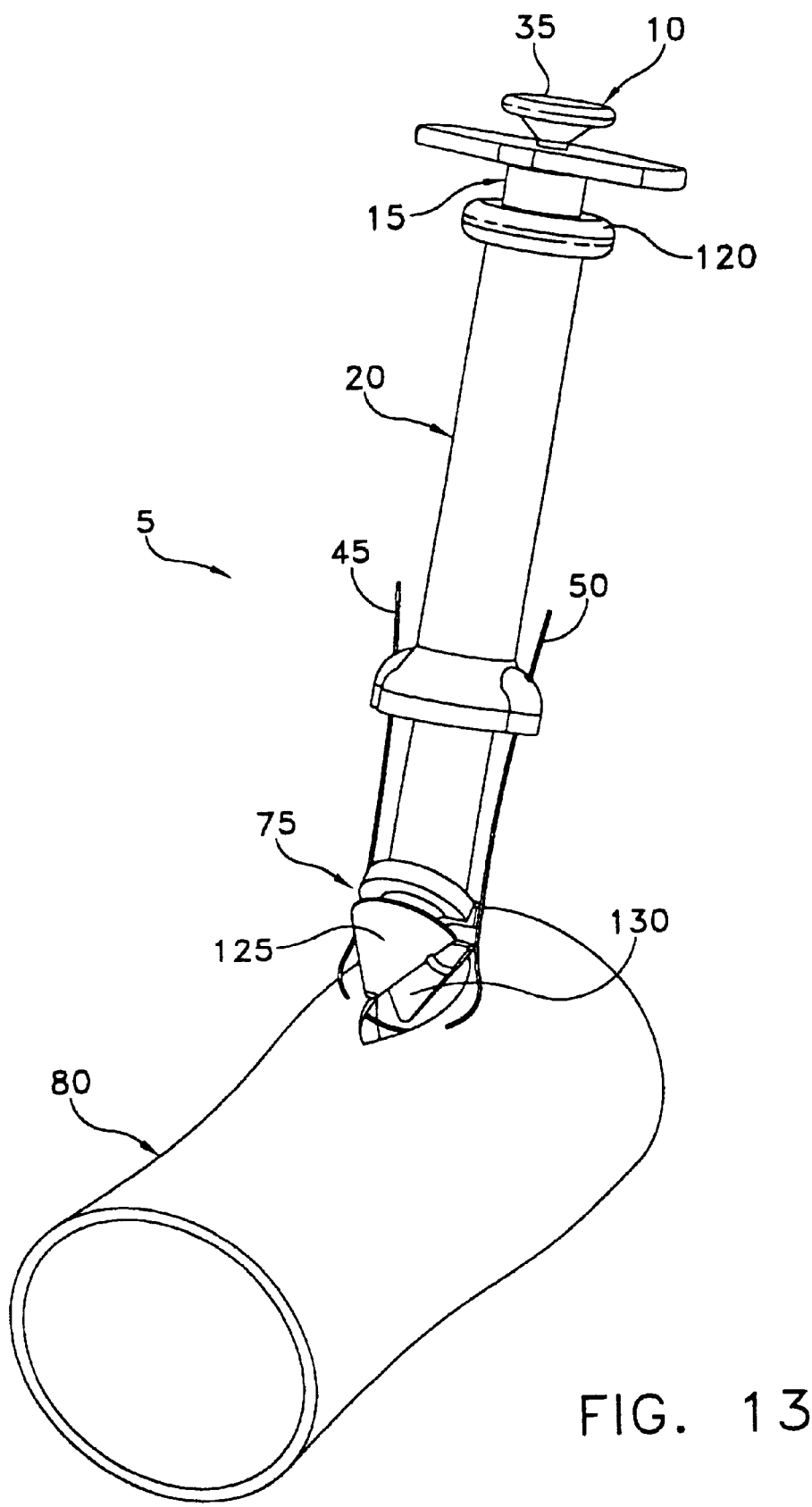

Wire channel 25 extends to the distal end of the housing 15, where the channel bifurcates into two, separate, diametrically-opposed channels 55, 60 (see FIG. 4) that turn outward at a point on the device that is located just underneath the edges of the hole 65 which is to be sutured (see, for example, FIG. 11).

Figure 8:
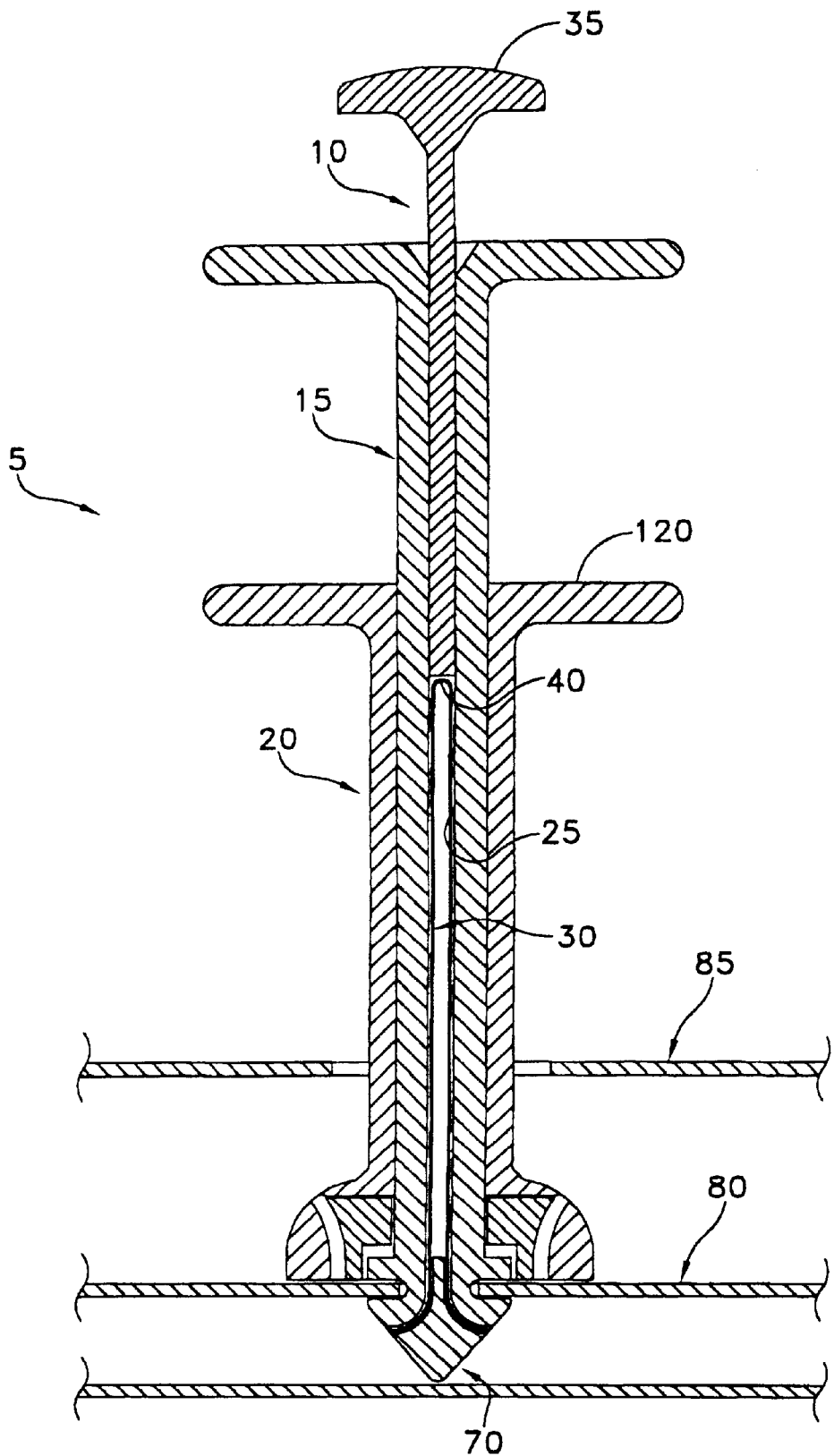

A tapered rounded protrusion 70 is formed at the distal end of housing 15 for insertion into the hole 65 which is to be sutured. The edges of hole 65 are located along the housing, in part, by a groove 75 that extends around the perimeter of the housing proximal to protrusion 70. The elasticity of typical physiological shell structures (e.g., arteries, veins, etc.), and the tight fit of the protrusion 70 into the hole 65, causes the walls of hole 65 to locate into groove 75 and thereby help position suture introducer 5 relative to the tissue (e.g., tissue 80) which is to be sutured. In this respect it should be appreciated that the tissue to be sutured (e.g., tissue 80) may be an interior structure such as an artery or vein which may in turn lie below the outside surface of another anatomical structure (e.g., skin 85) such as is shown in FIGS. 8 and 9.

Sleeve 20 slides along the outside of housing 15. The cross-sectional shapes of the sleeve's interior and the housing's exterior are preferably slightly elliptical so as to prevent relative rotation of the sleeve and housing with respect to one another; however, if desired, the cross-sectional shapes of the sleeve's interior and the housing's exterior can also be formed round if desired, such as is shown in FIG. 5. The distal end of the device has an internal step 90 (see FIGS. 3 and 4) that limits the forward motion of the sleeve relative to housing 15. At this limit position, the rounded protrusion 70 of the housing 15 extends beyond the end of sleeve 20. When protrusion 70 is inserted into the hole 65 which is to be sutured, the walls of tissue 80 not only locate into groove 75, but also sit against the end of sleeve 20 (see FIG. 8), thereby positioning the edges of the tissue adjacent to the diametrically opposite wire exit points of the bifurcated channels 55 and 60.

Figure 4:
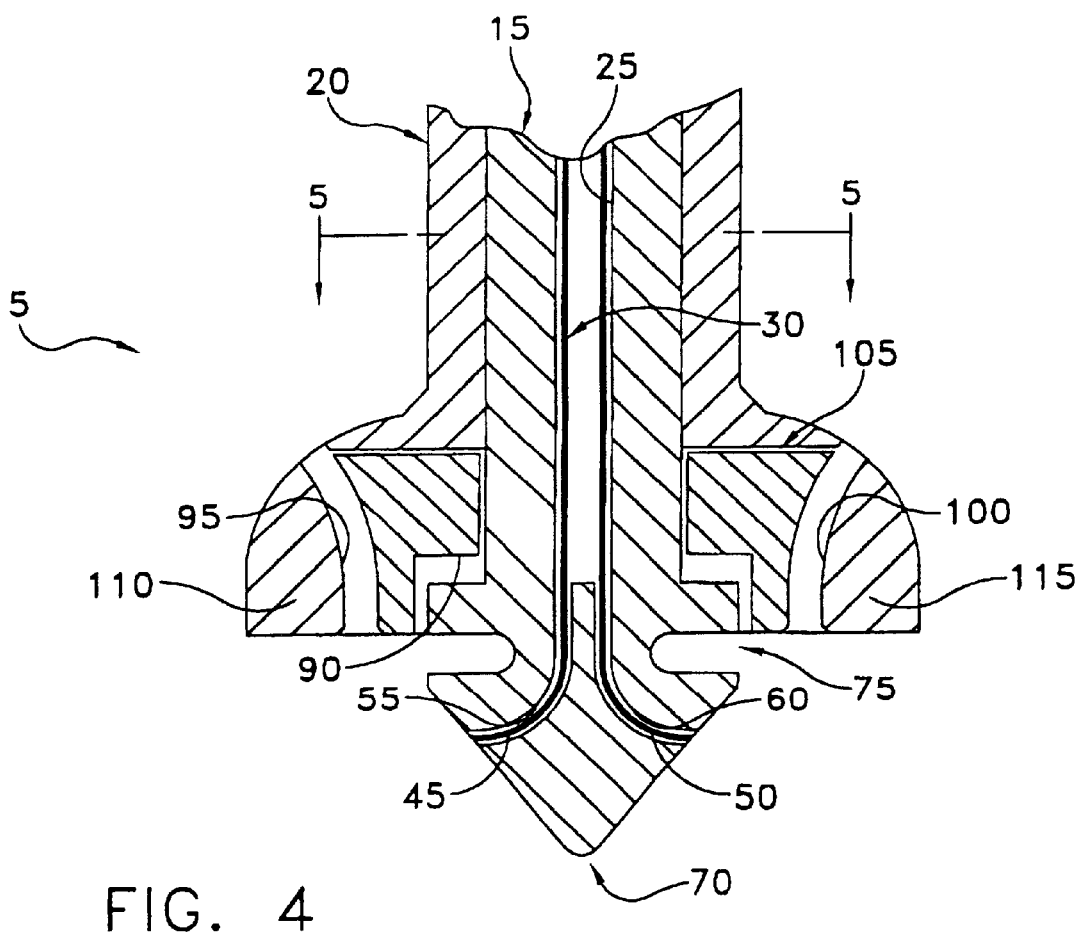
FIG. 4 is an enlarged sectional view of the distal end of the suture introducer shown in FIG. 3.
Figure 5:
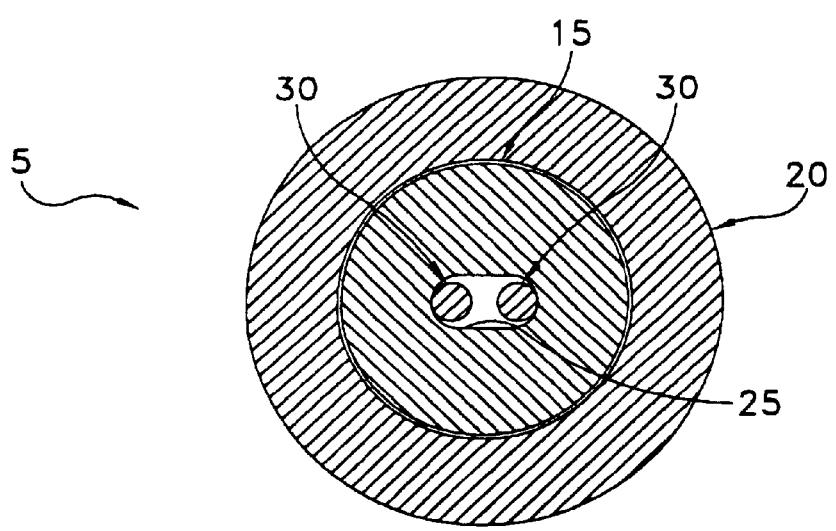
FIG. 5 is a sectional view taken along line 5—5 of FIG. 4.
Figure 6:
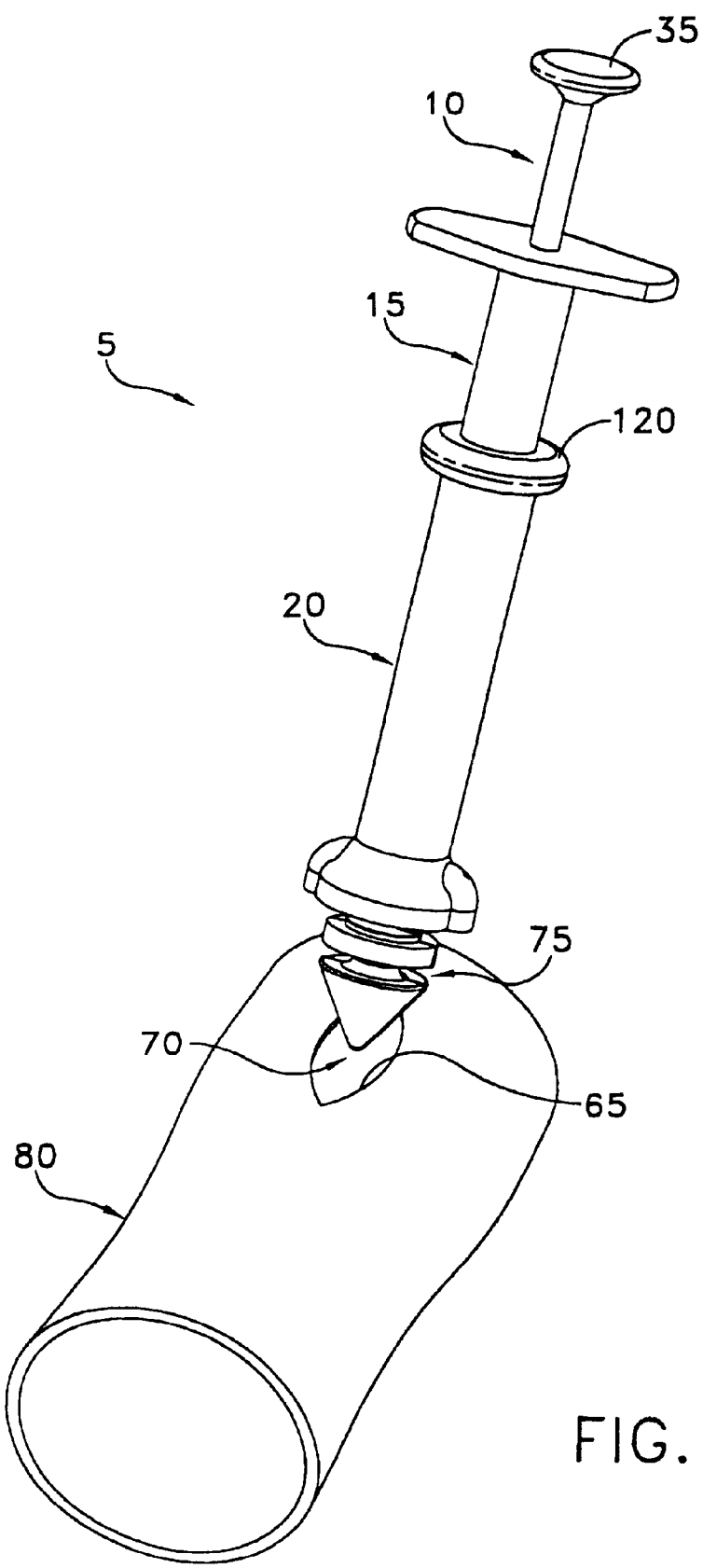
FIGS. 6–15 are a series of perspective and sectional views showing the suture introducer of FIG. 1 delivering suture to tissue.
Figure 7:
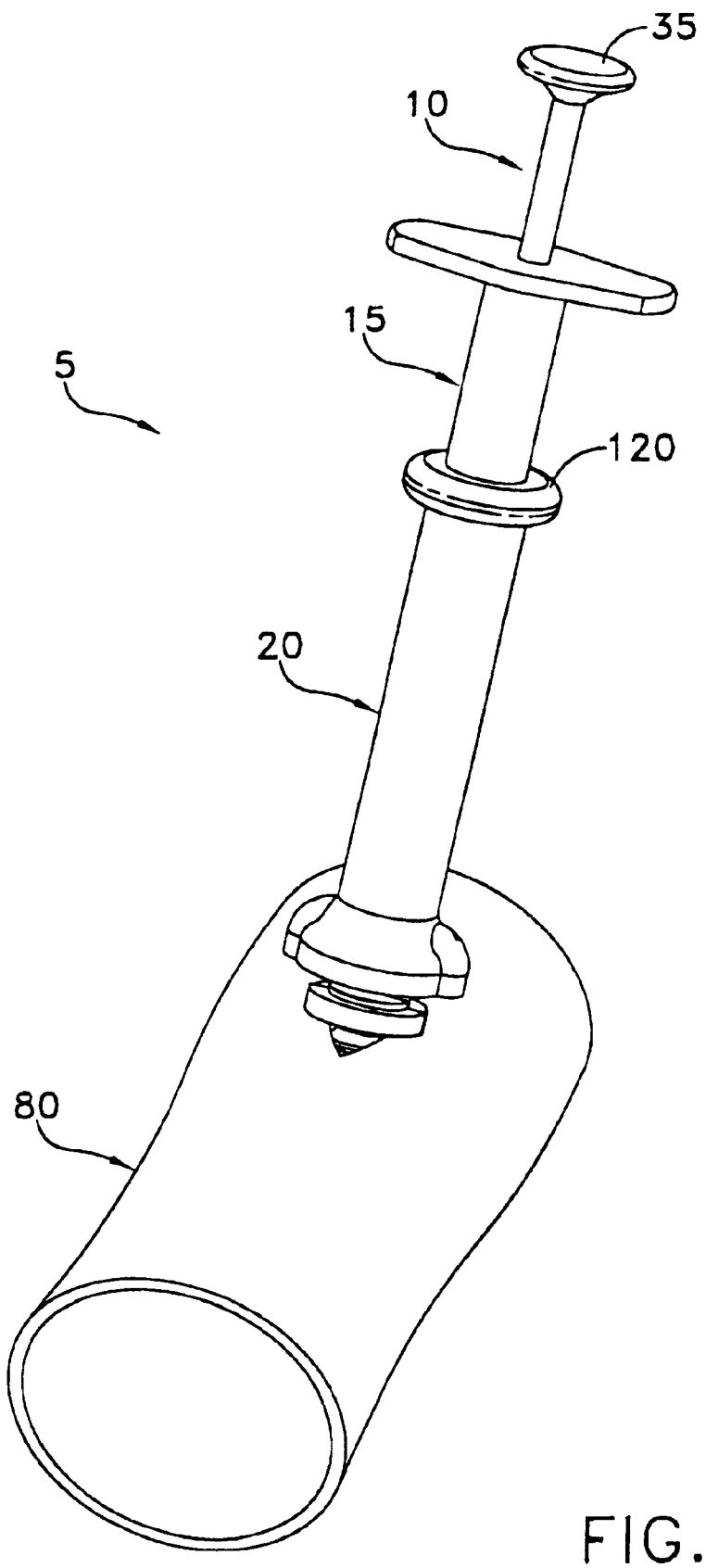
Figure 9:
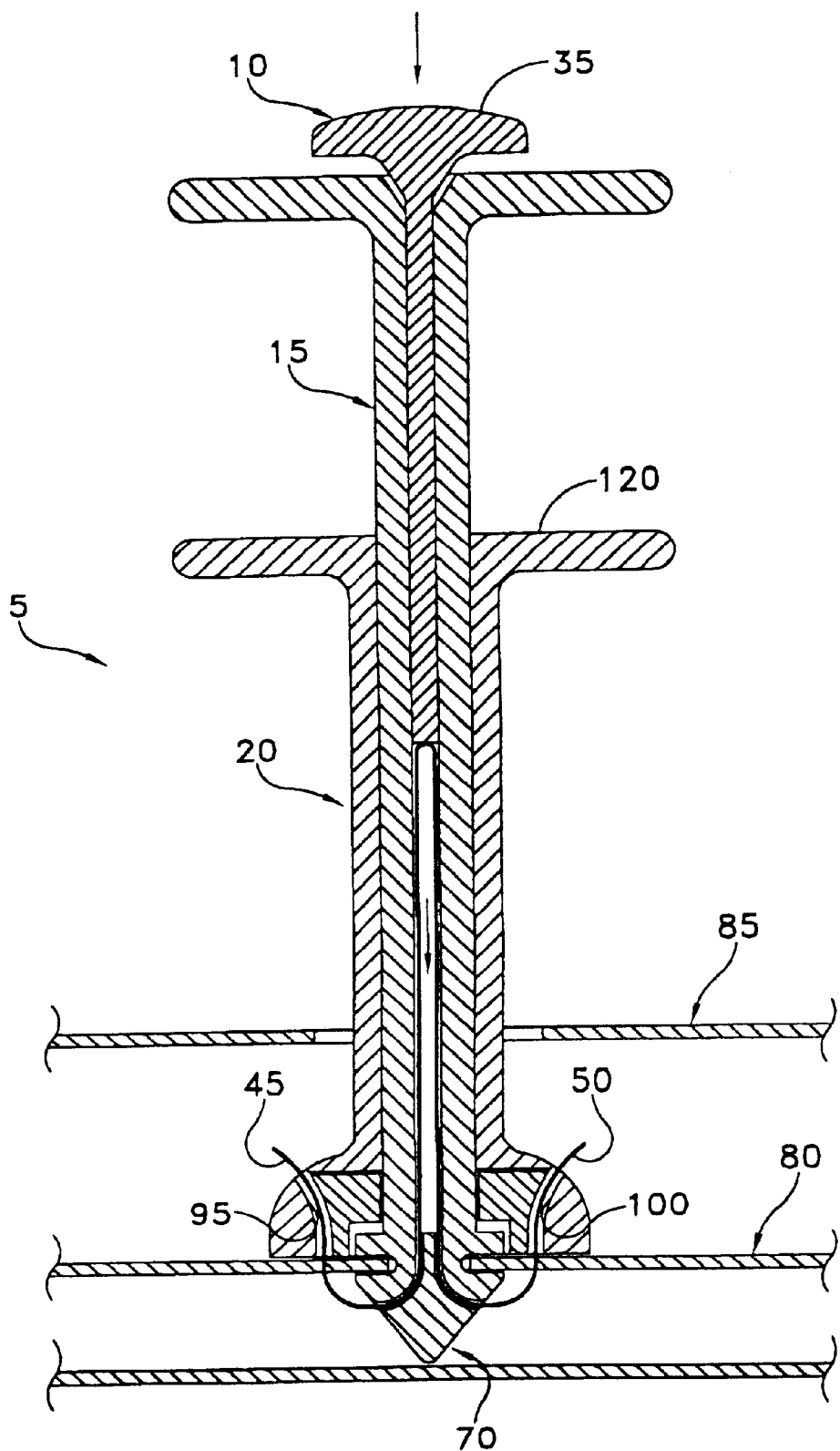
Figure 10:
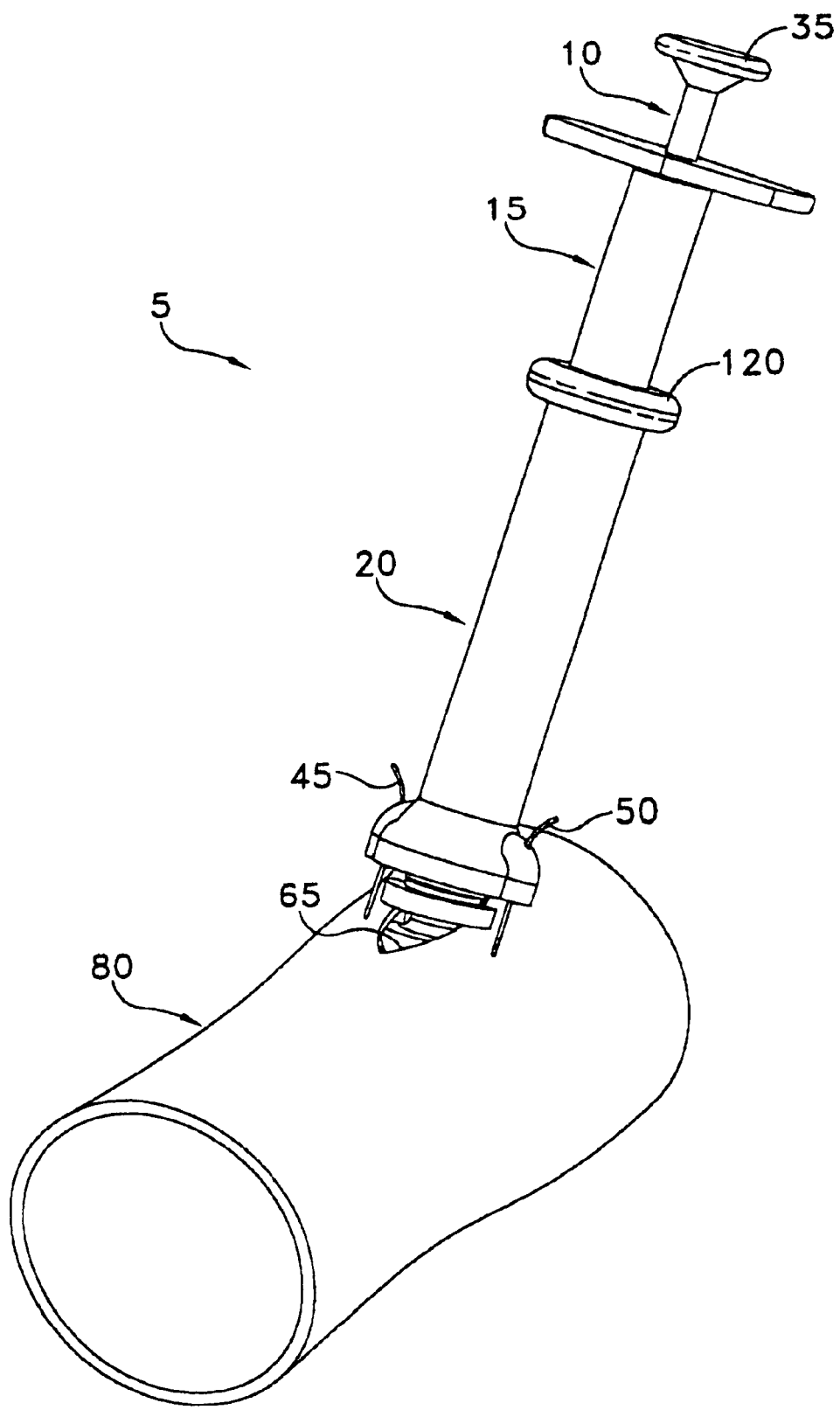

When wire suture 30 is deployed, the two distal ends 45, 50 of the wire move out of these exit points, through tissue 80, and finally into wire-receiving channels 95, 100 located in the distal end of sleeve 20 (see FIGS. 4 and 9). These channels 95, 100 are in line with the trajectory of the suture wire 30 as the wire penetrates the tissue 80. The channels 95, 100 not only receive the wire ends 45, 50 exiting the tissue but also hold onto those wire ends once the wire ends have entered the receiving channels 95, 100, whereby the wire ends can be pulled away from tissue 80, as will hereinafter be discussed in further detail.

Various means may be provided to hold onto the wire ends 45, 50 after they have entered the wire-receiving channels 95, 100. By way of example but not limitation, sleeve 20 may have an inner frictional member 105 (see FIG. 4), part of which forms the proximal walls of channels 95, 100. The inner frictional member 105 slides against housing 15 with some amount of resistance. The remainder of sleeve 20 is composed of two arms 110, 115 (see FIG. 4) that form the distal walls of channels 95, 100 and are connected to the distal end of sleeve 20. As a result of this construction, when sleeve 20 is retracted proximally with the wire ends 45, 50 in wire-receiving channels 95, 100, the friction of the inner frictional member 105 with housing 15 causes the channel walls to collapse on the wire ends and hold the wire ends to the sleeve as sleeve 20 is pulled proximally. FIGS. 9 and 11 show cross-sectional views of the wire-receiving channels 95, 100 in the open and closed configurations, respectively. Handle 120 (see FIG. 1) at the proximal end of sleeve 20 allows the user to manually pull the sleeve back, which in turn causes the captured suture wire to move with the sleeve. Sleeve 20 is pulled back from the surgical site, bringing the two wire ends 45, 50 with it.

Thus, by positioning the distal end of suture introducer 5 in the hole 65 in tissue 80, and by pushing down on plunger 10 and then pulling back on sleeve 20, the middle 40 of suture wire 30 will have been pushed down wire channel 25 and will lie in the wire channel at the base of the protrusion 70 located at the distal end of housing 15, and the two free ends 45, 50 of the suture wire will have been withdrawn proximally by sleeve 20. Thus, the two free ends 45, 50 of suture wire 30 will have been passed through tissue 80 and been moved away from the surgical site, but the middle portion 40 of suture wire 30 will still reside inside the distal end of housing 15.

In order to release middle portion 40 of suture wire 30 from housing 15, protrusion 70 is split into two portions, a first portion 125 (FIG. 13) and a second portion 130. First portion 125 and second portion 130 are connected together by a living hinge. The interface of the split moves along wire channel 25 so that when the protrusion tip is separated into its two portions, the middle section 40 of suture wire 30 can be pulled from wire channel 25. The living hinge biases the two portions 125, 130 away from one another. Sleeve 20 normally fits over this area of protrusion 70 and holds the two portions 125, 130 of the protrusion together. The living hinge is located even with or, preferably, proximal to, the point where the wire ends 45, 50 exit protrusion 70 of housing 15.

Figure 14:
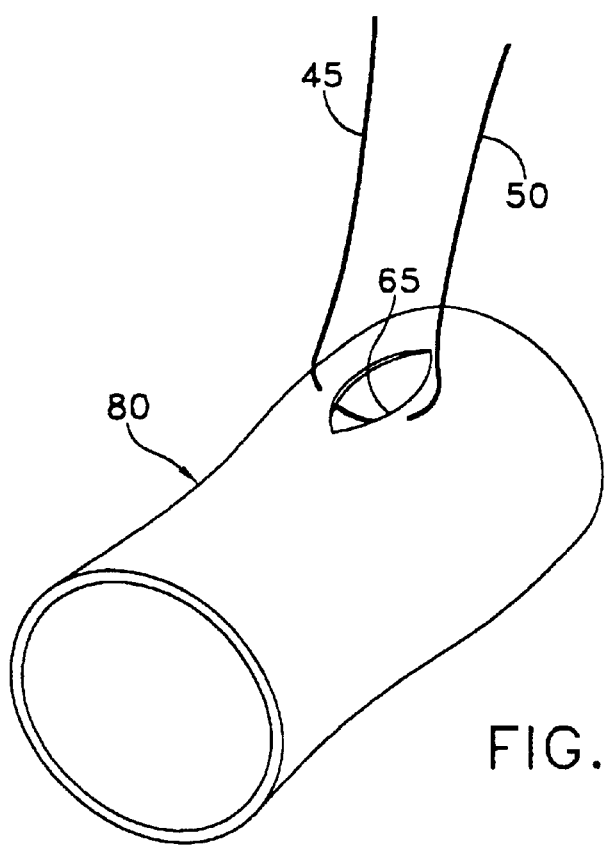

After sleeve 20 has been withdrawn to pull the suture ends 45, 50 proximally (see FIGS. 12 and 13), the two protrusion portions 125, 130 spring apart, thereby exposing wire channel 25 and freeing the middle section 40 of suture wire 30 from housing 15, so that suture introducer 5 can be withdrawn from the surgical site (see FIG. 14).

Figure 15:
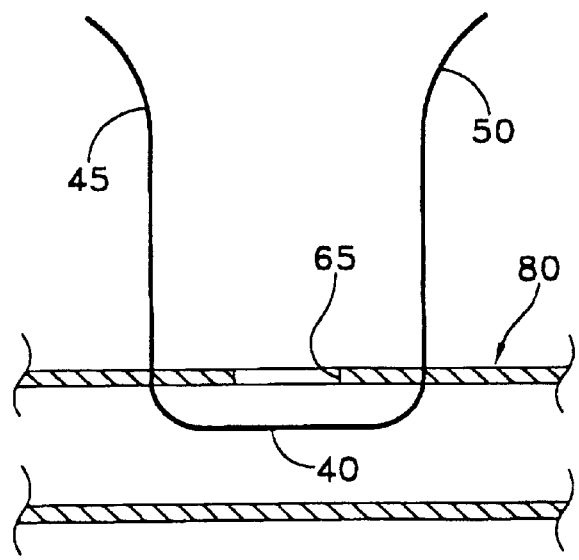

At this point suture wire 30 will extend through opposing sides of hole 65 (see FIGS. 14 and 15). The two wire ends 45, 50 are now ready to be twisted together using the aforementioned suture tensioner so as to close and secure the hole 65 in tissue 80.

Looking next at FIGS. 16–24, there is shown a suture tensioner 135 formed in accordance with the present invention. Suture tensioner 135 generally comprises two concentric shafts, an outer support tube 140 and an inner twisting shaft 145.

Figure 16:
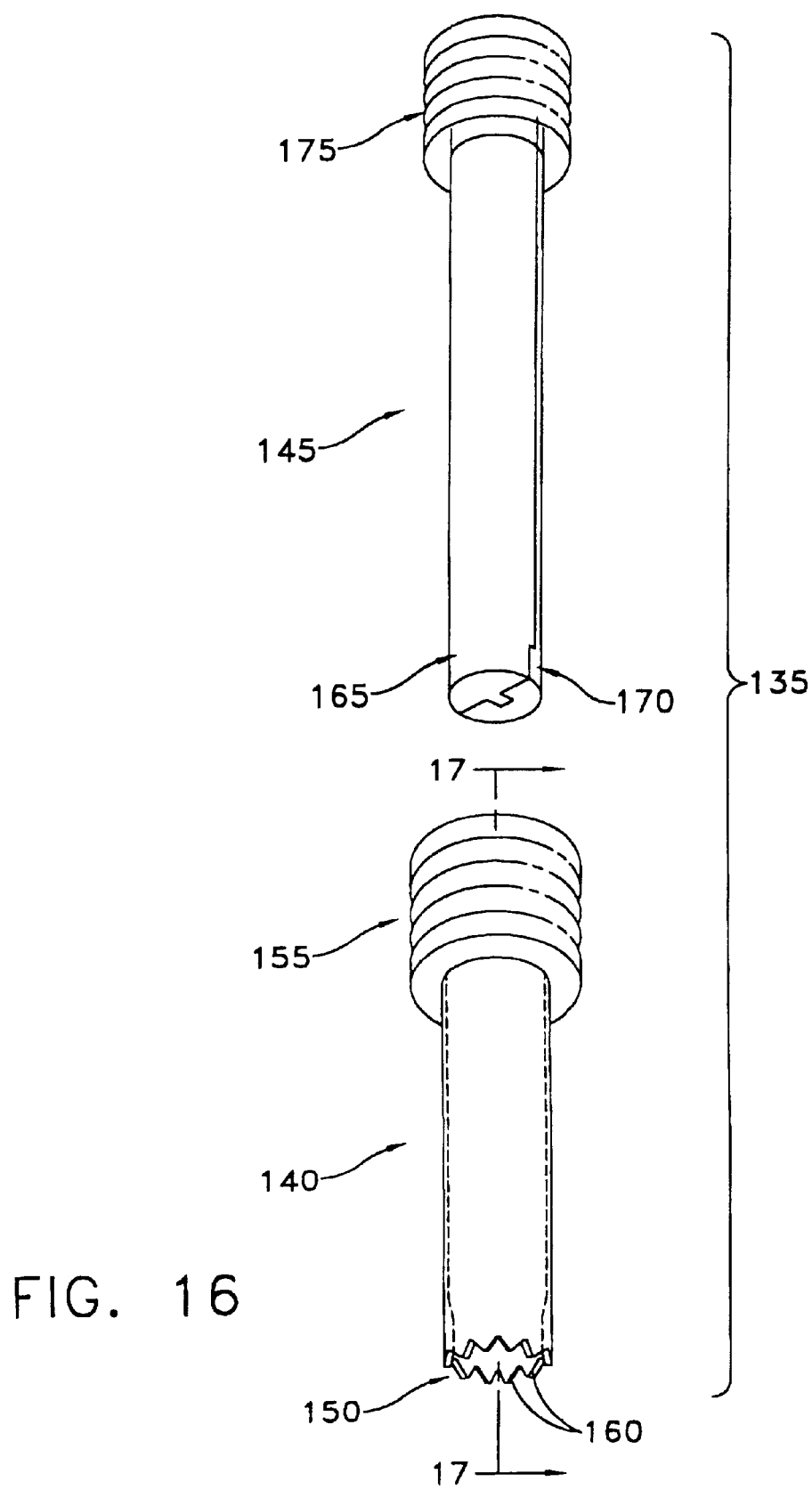
FIG. 16 is a perspective view of a suture tensioner formed in accordance with the present invention.
Figure 17:
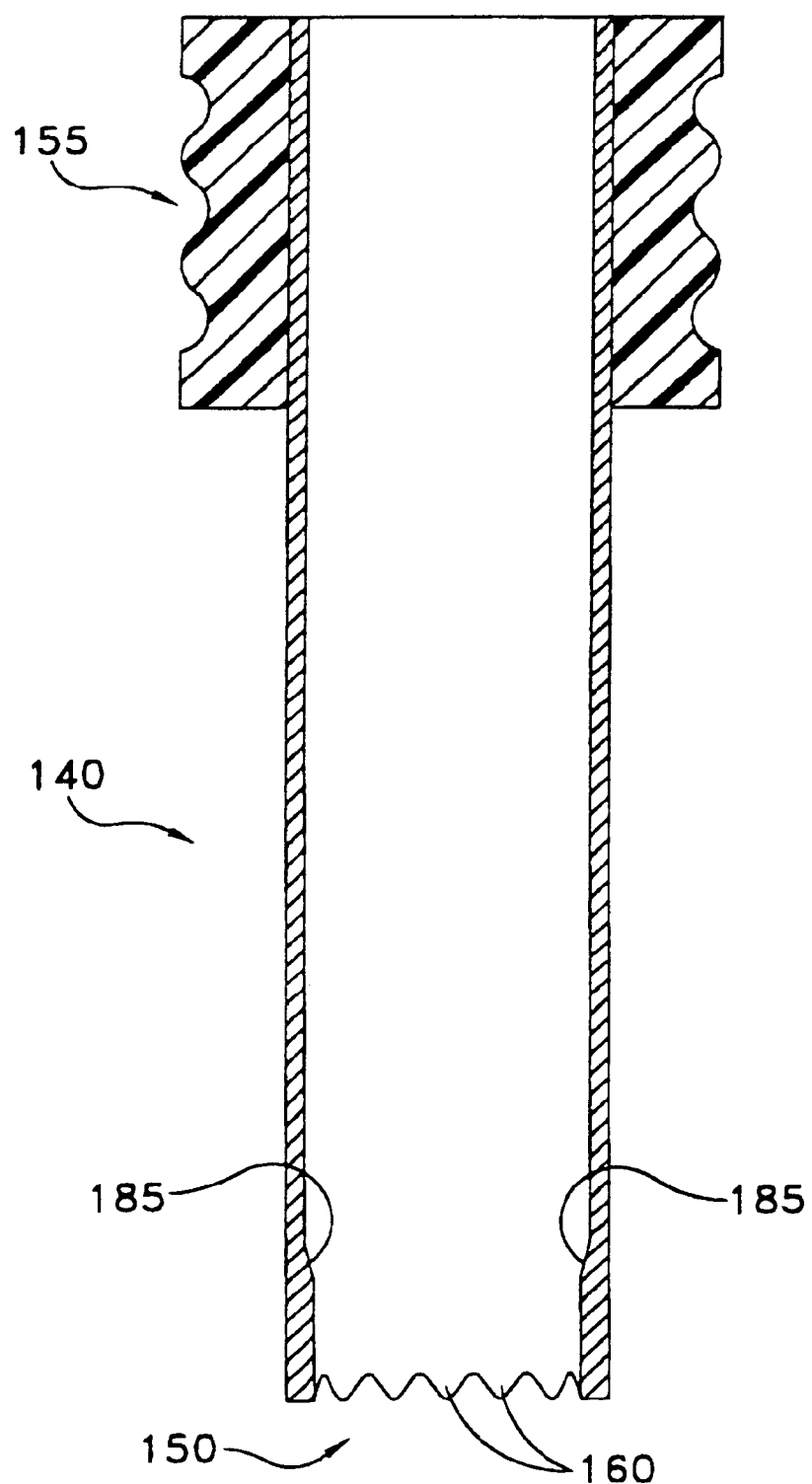
FIG. 17 is a sectional view of the suture tensioner's support tube.
Figure 18:
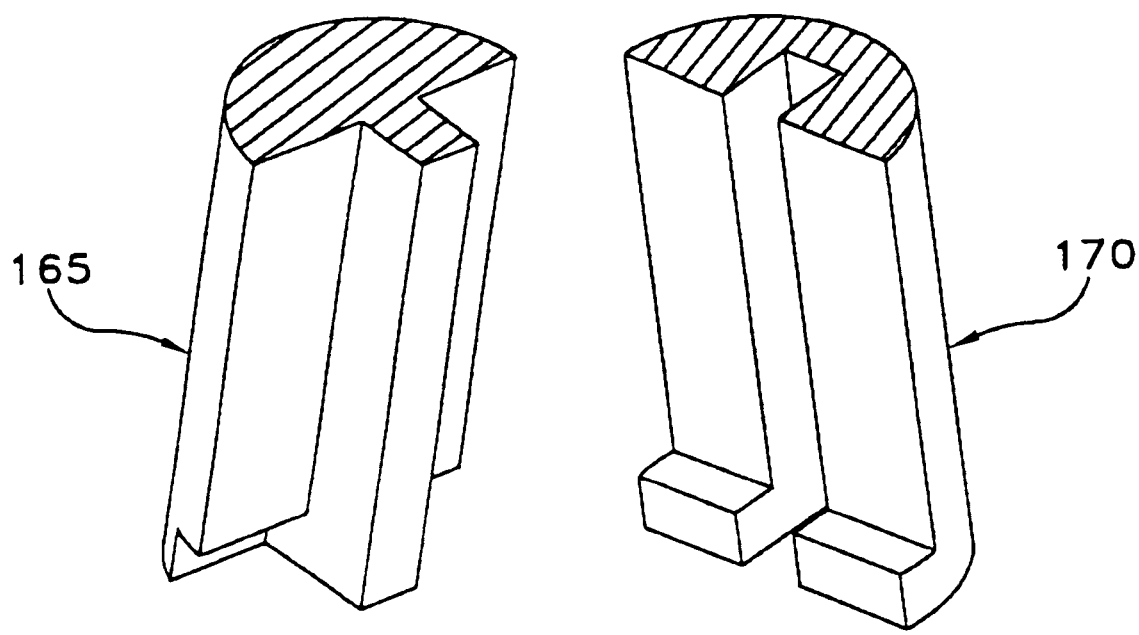
FIG. 18 is a partial schematic view of the suture tensioner's twisting shaft.
Figure 19:
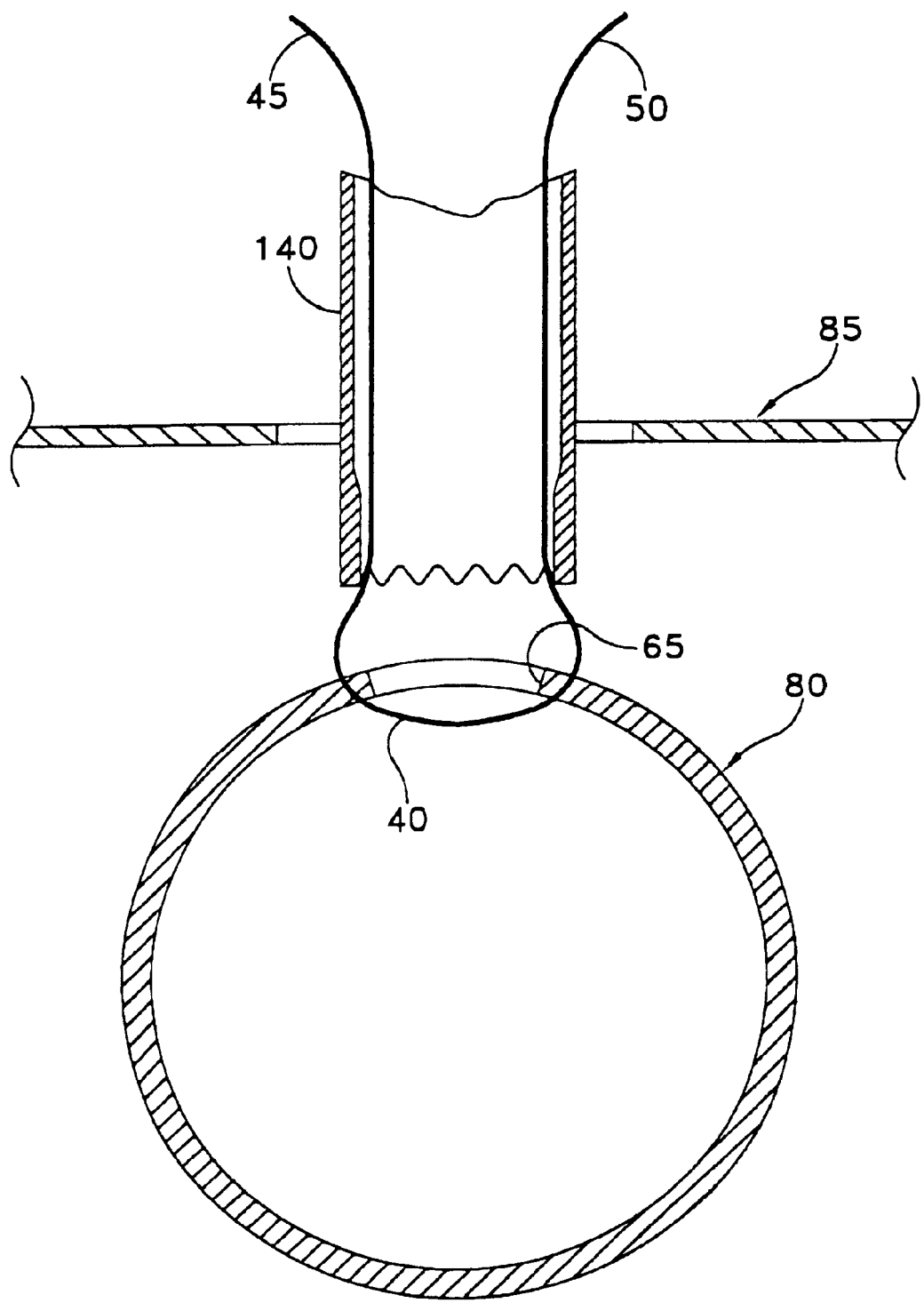
FIGS. 19–24 are a series of sectional and perspective views showing the suture tensioner of FIG. 16 gathering, supporting, twisting and cutting the two free ends of a length of suture wire.
Figure 20:
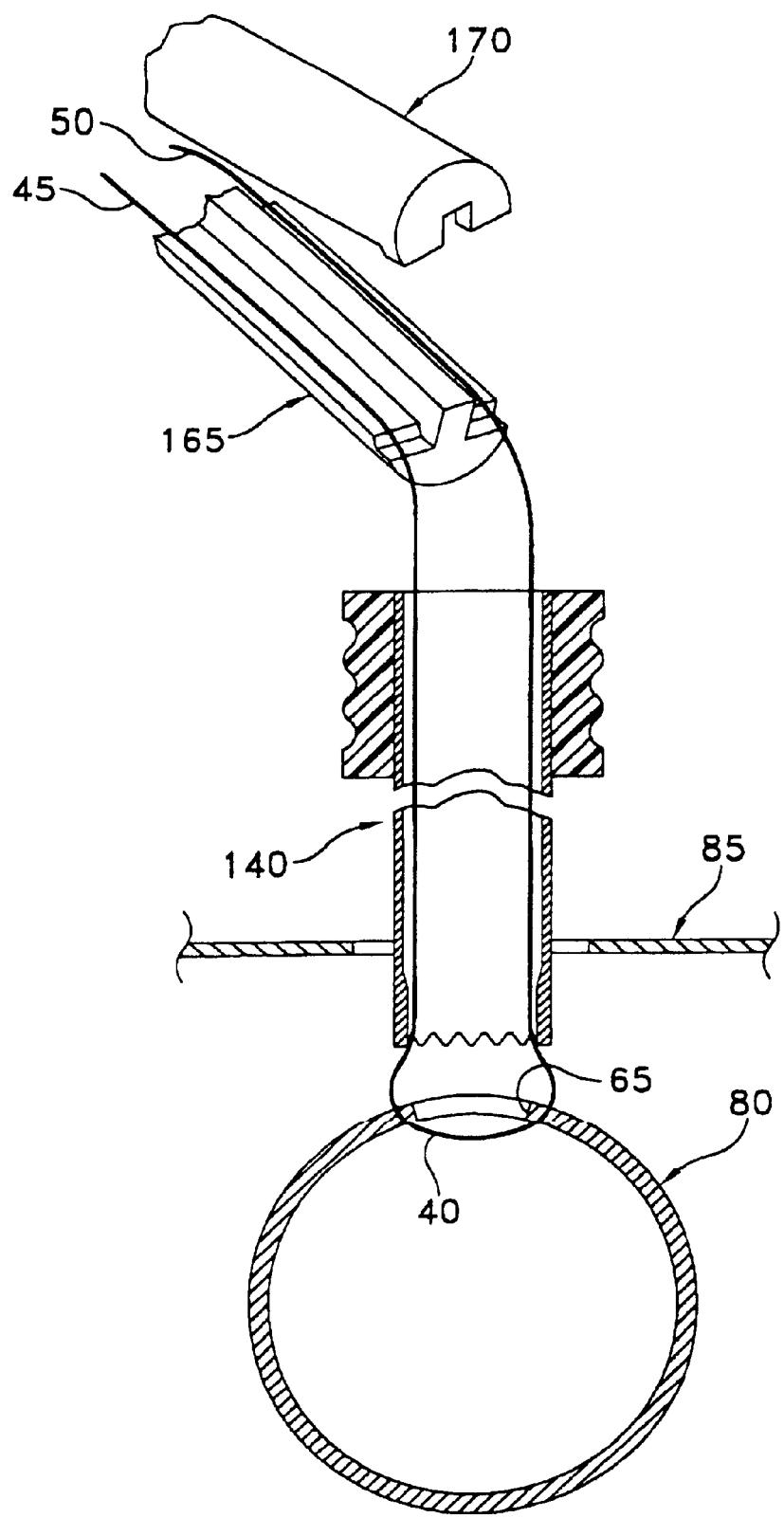

As shown in FIGS. 16 and 17, support tube 140 has a sawtooth pattern 150 along the distal end of the shaft and a handle 155 at the proximal end. The user feeds the two free ends 45, 50 of suture wire 30 into the distal end of support tube 140 (i.e., through the troughs of the crown) and then up through the shaft and out the proximal end. Then the distal end of the support tube is passed down to the closure site while the two suture ends 45, 50 are pulled firmly proximally by the user (see FIGS. 19 and 20). In the embodiment shown in FIGS. 19 and 20, because the outside diameter of support tube 140 is smaller than the separating distance between the exit points of the suture from tissue 80, the suture wire will be forced between individual teeth 160. Teeth 160 will support suture wire 30 and prevent the suture wire from tugging on tissue 80 during wire twisting. Light tactile feedback is all that is required to position support tube 140 onto the two free ends 45, 50 of suture wire 30, enabling this to be easily accomplished down a blind hole.

Figure 21:
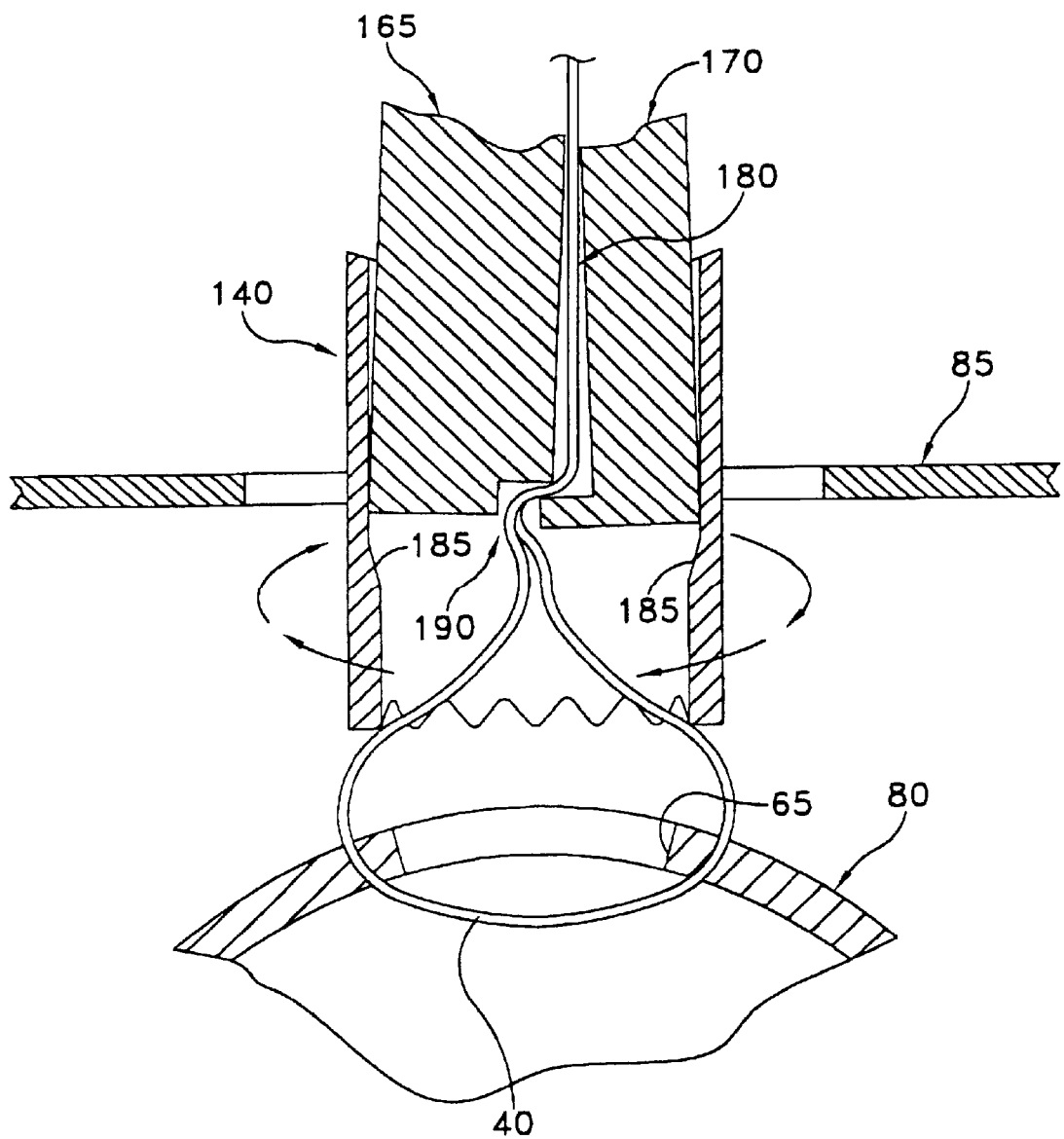
Figure 22:
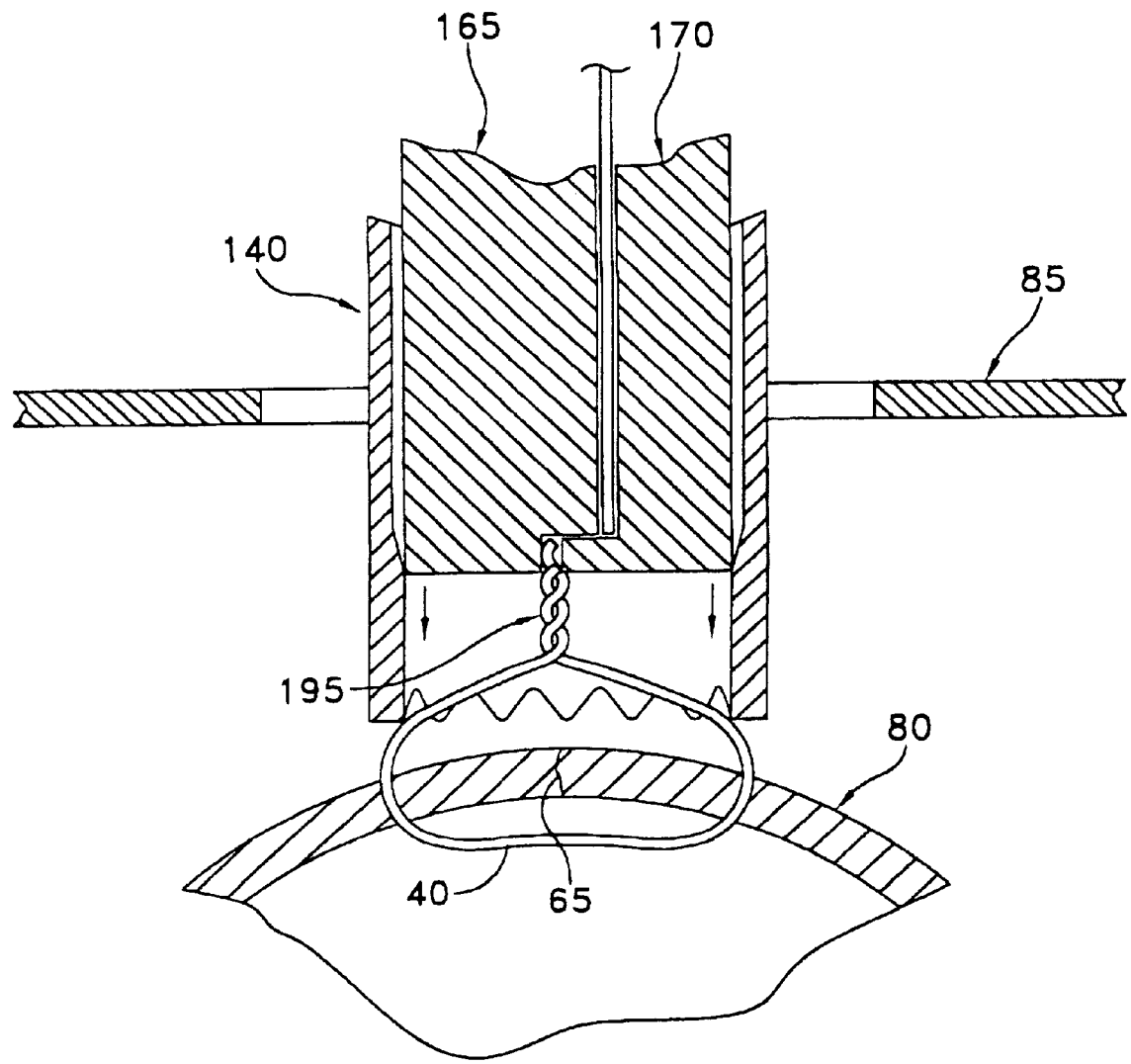
Figure 23:
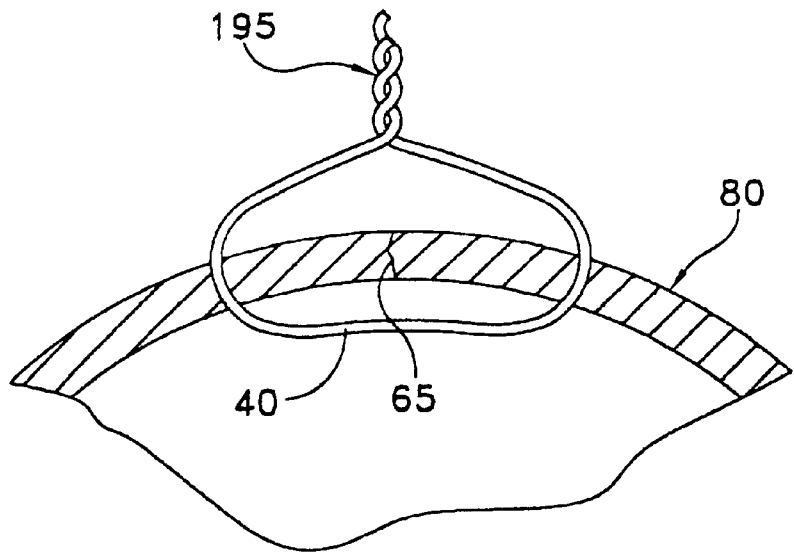
Figure 24:
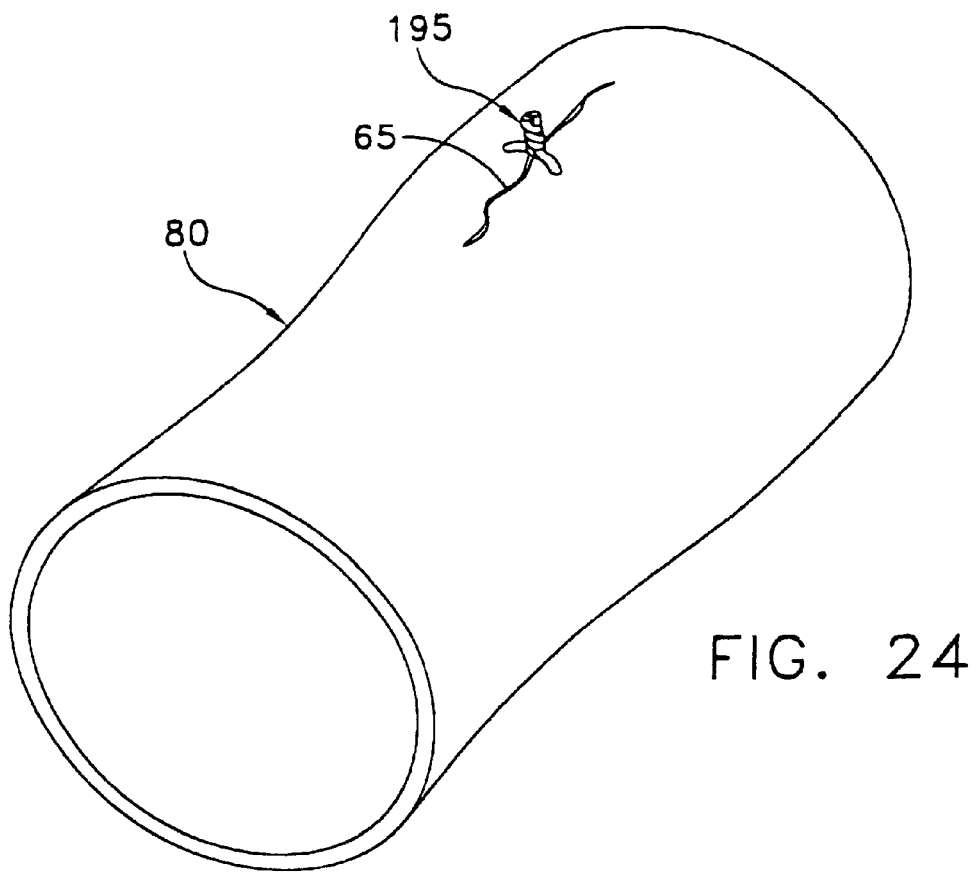

Twisting shaft 145 is partially constructed of two halves 165, 170 that pivot near a handle 175 located at the proximal end of the shaft (see FIG. 16). When the two halves 165, 170 are brought together, they form two channels 180 (one of which is shown in FIG. 21) that run the length of the twisting shaft. The channels 180 are open along approximately diametrically opposite sides of the shaft. The two free ends 45, 50 of wire suture 30 are each inserted into a channel 180 and the twisting shaft 145 is fed down along the wires and into the interior of support tube 140. At the end of support tube 140 there is a narrowing of the internal diameter at 185 (see FIGS. 17 and 21) that arrests any further unforced forward advance of twisting shaft 145 relative to the support tube 140 (see FIG. 21). At this relative position, the distal end of twisting shaft 145 is only a short distance from where the ends of the suture wire 30 emerge from tissue 80 and, as such, require only a limited number of twists in order to bring the opposing edges of the tissue together. Because the channels 180 of twisting shaft 145 maintain the wires a distance from the center of rotation of the shaft, twisting shaft 145 will cause the wires to twist about each other along the length between tissue 80 and the distal end of the twisting shaft. Again, tactile feedback will indicate when the wires have been twisted enough to close the distal loop of wire and hence join the edges of the tissue.

A spring (not shown) normally limits the closure of the two twisting shaft halves 165, 170 so that when the shaft is inserted into support tube 140 and encounters the distal narrowing 185 of the internal diameter of support tube 140, twisting shaft 145 will slightly resist any further advance of the twisting shaft 145 until the user is ready to cut the wires. The two halves 165, 170 of the twisting shaft create a step offset 190 (see FIG. 21) in the channels 180 at the distal end of twisting shaft 145, causing a slight deviation in the wire path when the halves are closed to the wire twisting position (see FIG. 21). When twisting shaft 145 is thereafter further advanced into the narrowing internal diameter of support tube 140, the two halves 165, 170 of the shaft will be urged together, causing the step offset 190 of the channels to slide past each other and shear the wires just above the twisted section 195 of the wire (see FIG. 22). Then both support tube 140 and twisting shaft 145 are removed, leaving the hole 65 closed and secured by the twisted wire knot 195 (see FIGS. 23 and 24).

Figure 25:
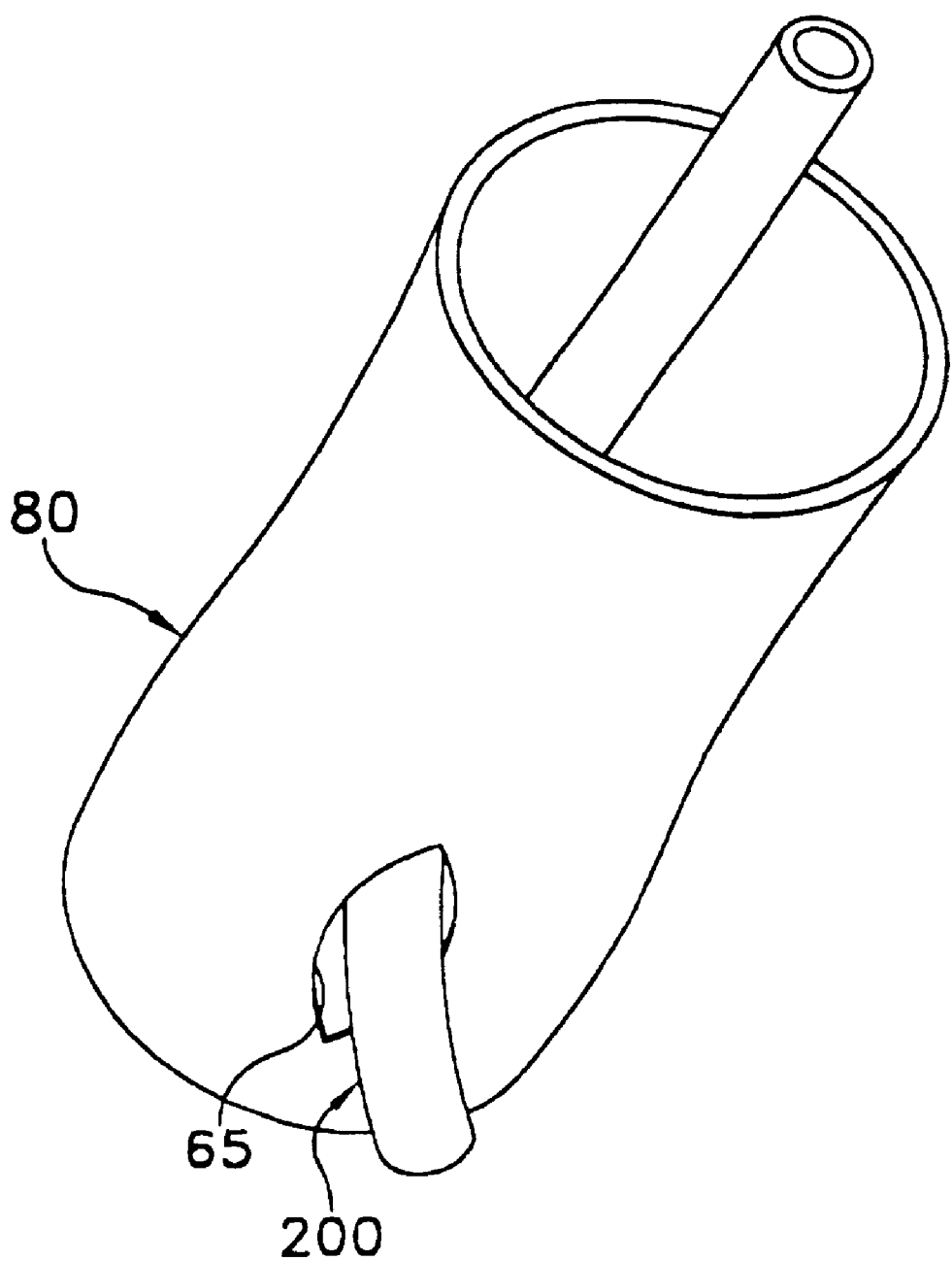
FIG. 25 is a perspective view showing a catheter extending through a vascular structure (e.g., a femoral artery)
Figure 26:
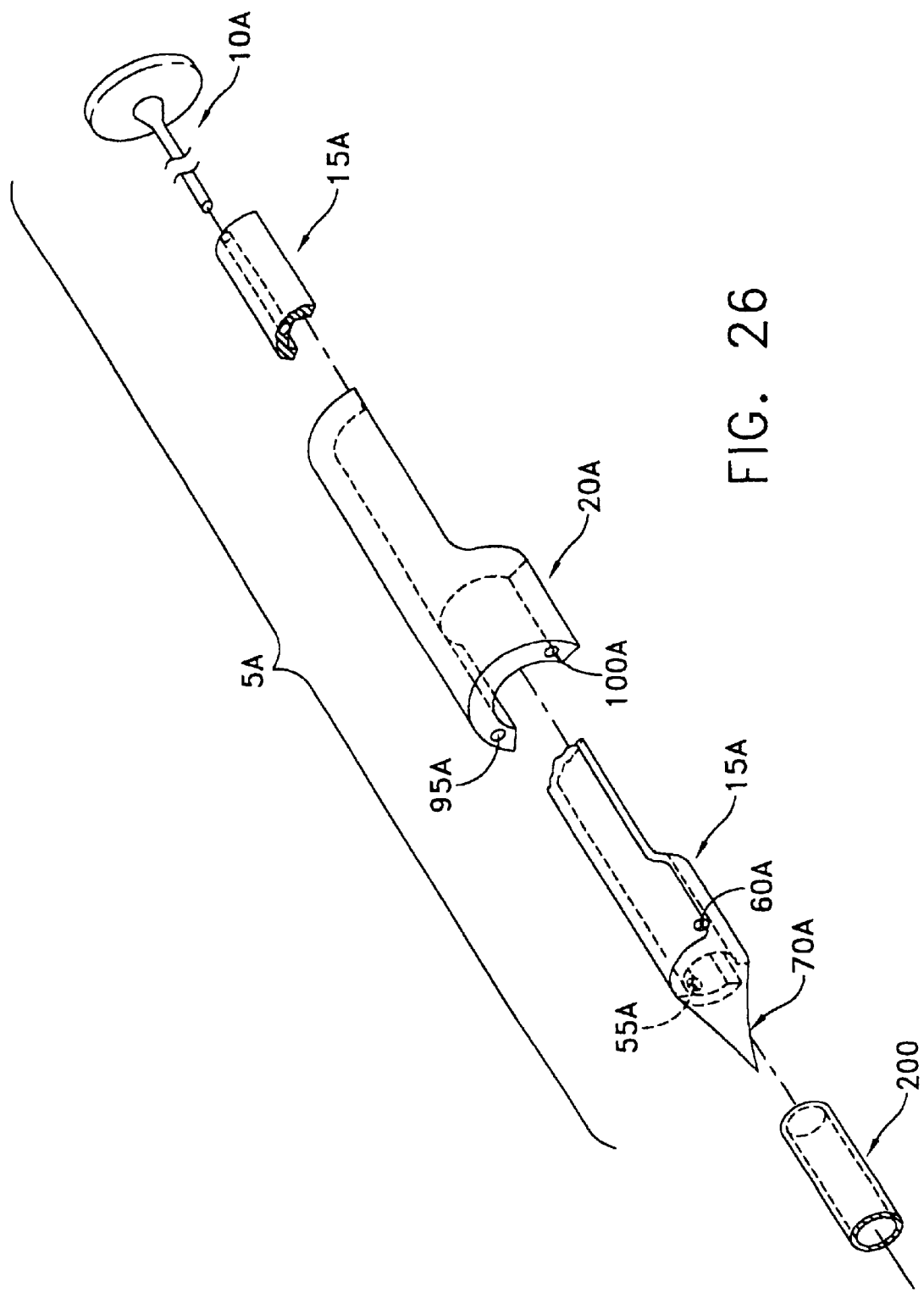
FIG. 26 is an exploded perspective view of an over-the-catheter suture introducer which is adapted to ride along the catheter so as to position the suture introducer at the hole in a vascular structure.
Figure 29:
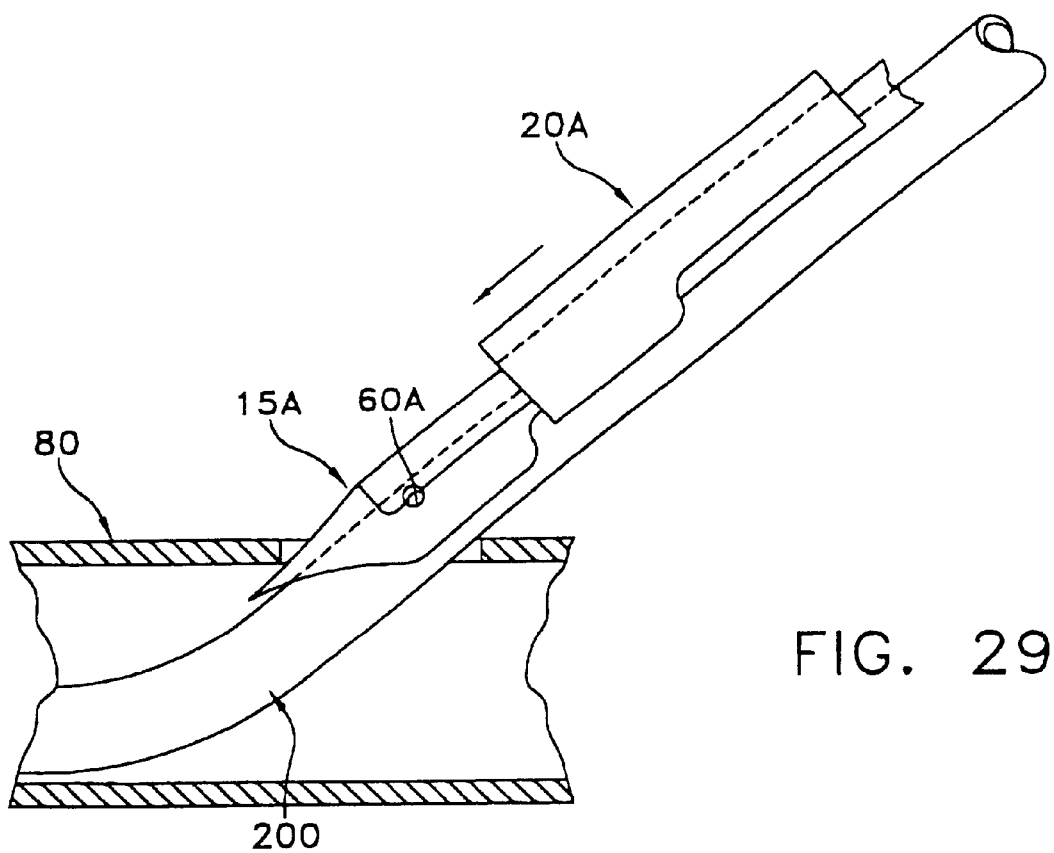
FIGS. 29–33 are a series of schematic views showing the over-the-catheter suture introducer of FIG. 26 delivering suture to a vascular structure.
Figure 30:
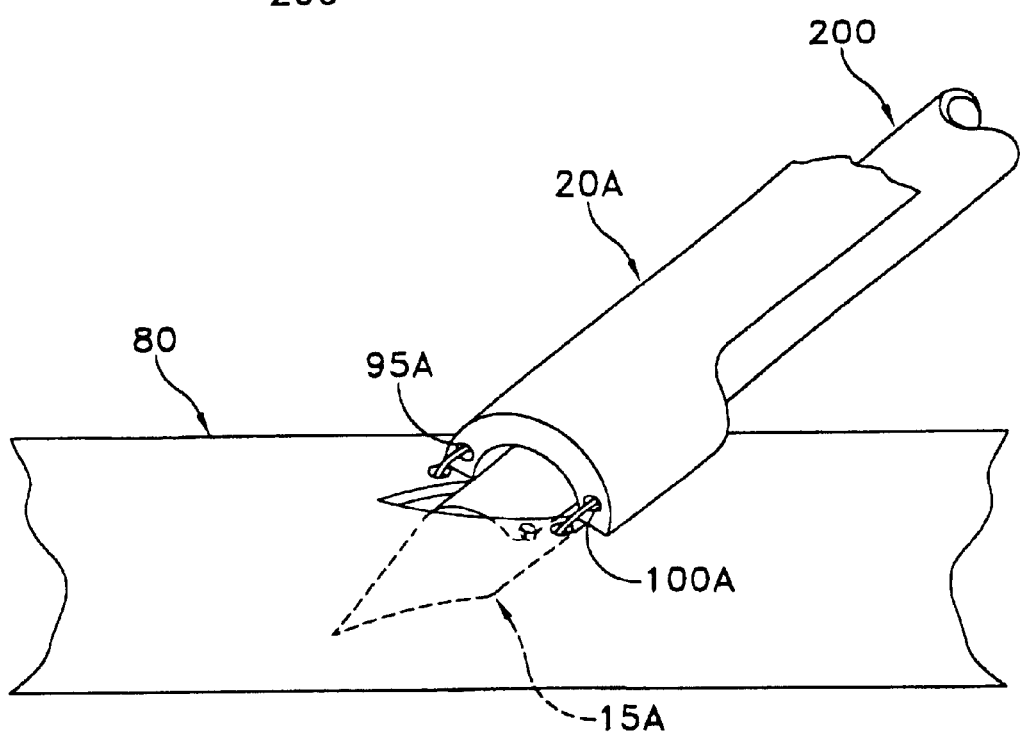
Figure 31:
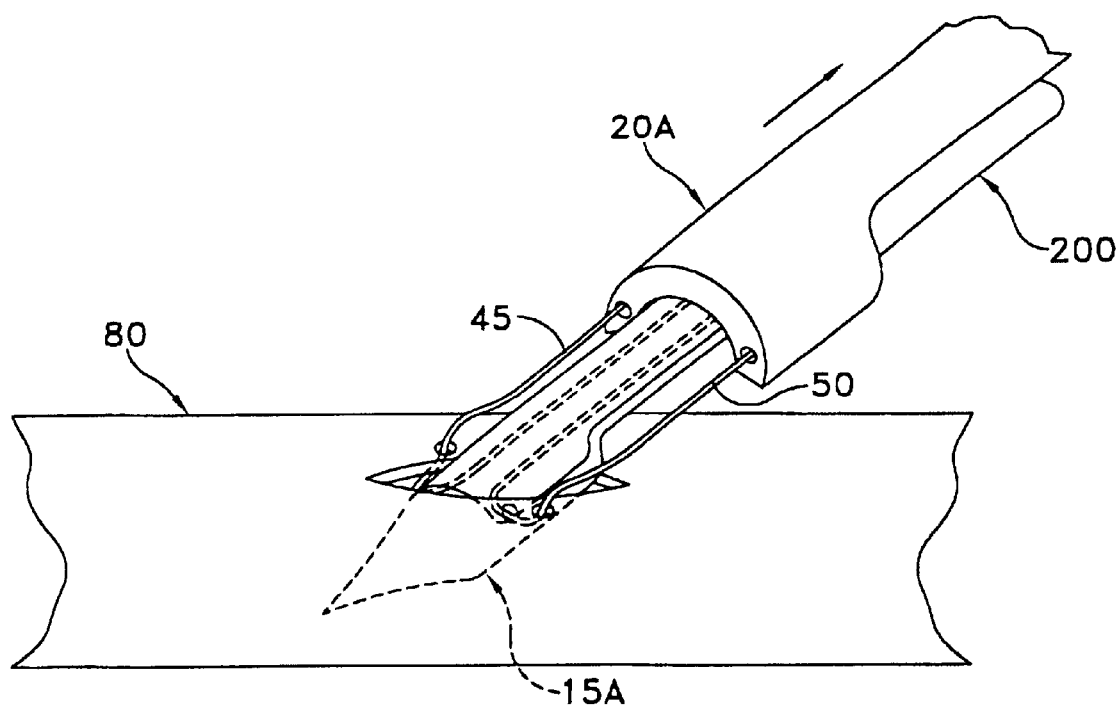
Figure 32:
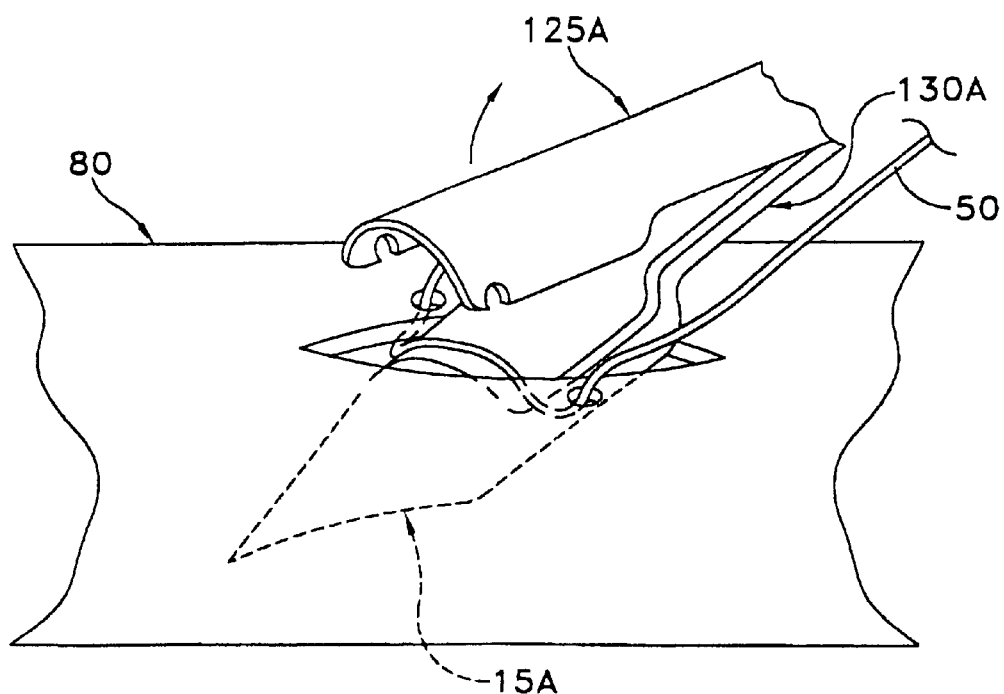
Figure 33:
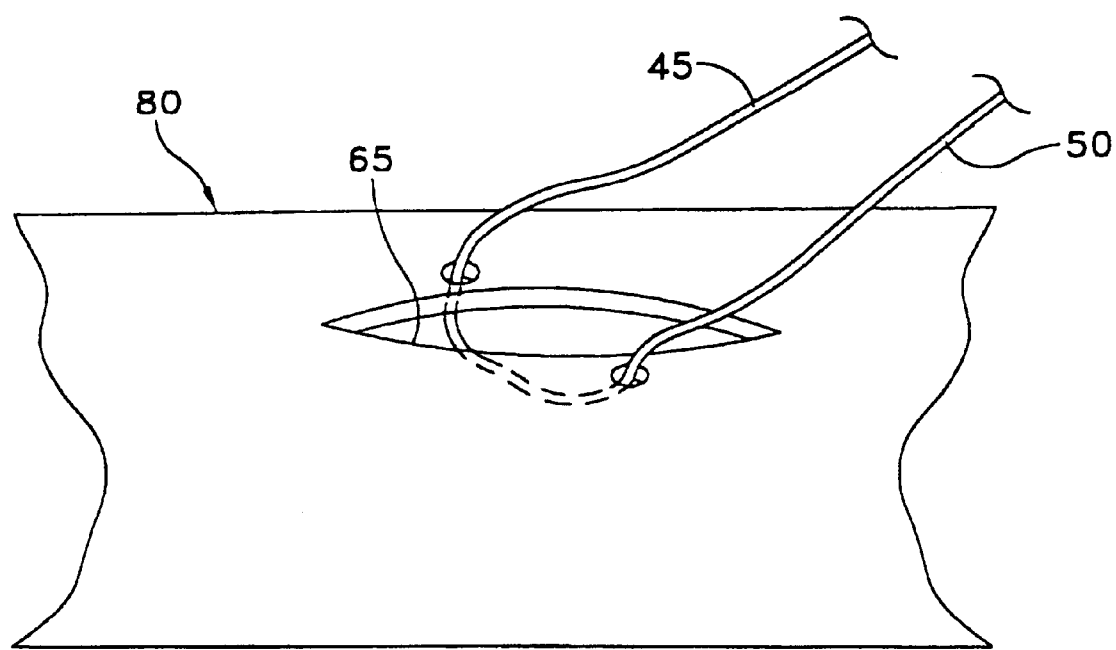

A common situation that requires the closure of a remote anatomical shell structure occurs when a catheter 200 is inserted into the femoral artery 80 through the opening 65 (see FIG. 25). This artery is located relatively far below the surface of the leg so that it can be difficult to suture closed the hole 65 left by the catheter 200 without making a much larger incision into the skin. Furthermore, it is preferable to put the sutures in place before catheter 200 is removed from the artery and then tie the sutures down quickly after the catheter is removed. This has the advantage of reducing blood loss and, by leaving the catheter 200 in place until the sutures are positioned, offers the opportunity of using the catheter to bring the closure device to the edges of the hole 65 in the arterial wall 80.

FIGS. 26–32 show a modified suture introducer 5A that comprises a modified housing 15A that contains suture wire 30 in channels 25A, 55A and 60A that direct it to the tissue as before, but the shape of housing 15A allows it to slip over catheter 200 and be pushed along its length. The distal tip of housing 15A has a sharp tapered point 70A that hugs the surface of the catheter such that when the tip 70A reaches the hole 65 in the artery 80, the housing 15A wedges itself between the catheter and the walls of the hole. When this resistance is felt, the housing 15A is pushed slightly further before the taper at the front of the housing prevents any further advance. The exit points of the wire channels 55A, 60A are now under diametrically opposite edges of the hole 65 in the artery 80. Wire advance plunger 10A is pushed forward, deploying wire ends 45, 50 through the tissue and into wire receiving channels 95A, 100A of the sleeve as before. As the sleeve 20A is pulled back, it allows the housing components 125A and 130A to split (FIG. 32) along a surface that exposes the wire channels, thus allowing the wire to be freed from the device. As both housing 15A and sleeve 20A are pulled back, the loop of the wire locates itself in the arterial lumen and as the wire ends 45, 50 are pulled, the edges of the hole 65 are drawn closer to each other. At this point suture introducer 5A is removed from the surgical site and the aforementioned suture tensioner 135 is used as before to twist and cut the wires.

Wire suture offers the advantage of acting as its own needle and provides the ability to form a knot that can be easily tied and tensioned. These attributes, combined into devices that can locate remote tissue edges, provide an efficient means to close inaccessible surgical openings.

As used herein, the term "suture wire" is intended to mean any filament-like element consistent with the present invention. By way of example but not limitation, suture wire may comprise a metal (e.g., stainless steel, titanium, Nitinol or other shape memory alloy, etc.), a plastic (e.g., polypropylene, polyimide, etc.), or other materials or combinations of materials.

What is claimed is:

1. A suture introducer comprising:

an elongated housing having a proximal end and a distal end, a first channel extending distally through said housing, and second and third channels communicating with said first channel and opening on the exterior of said housing;

said first channel being sized to receive the midsection of a loop of suture, and said second and third channels each being sized to receive a free end of the same loop of suture, and said second and third channels being configured so that when the midsection of a loop of suture is positioned in said first channel and one free end of the same loop of suture is positioned in each of the second and third channels, and said housing is positioned in tissue, pushing distally on the midsection of the loop of suture will cause the two free ends of the same loop of suture to exit the second and third channels so as to penetrate the tissue;

said elongated housing being hinged so as to selectively release the midsection of the loop of suture.

2. A suture introducer according to claim 1 wherein said second and third channels are configured so that the two frees ends of suture will be directed proximally after they exit said second and third channels.

3. A suture introducer according to claim 1 wherein suture introducer further comprises first and second suture gripping and transporting mechanisms, wherein said first and second suture gripping and transporting mechanisms are each adapted to (i) grip one free end of the loop of suture after that free end exits said housing and passes through the tissue, and (ii) transport that free end of the loop of suture proximally.

4. A suture tensioner comprising:

a support tube having a proximal end and a distal end, said support tube having a first larger diameter at its proximal end, a second smaller diameter at its distal end, and a transition section therebetween; and a twisting shaft having a proximal end and a distal end, said twisting shaft comprising a pair of elements pivotally connected together at their proximal ends;

said twisting shaft being configured so that (i) when said distal end of said twisting shaft is positioned in said first larger diameter region of said support tube, said twisting shaft can slidably receive a pair of suture ends, (ii) when said distal end of said twisting shaft is thereafter positioned in said transition section of said support tube, said twisting shaft can grip that pair of suture ends, and (iii) when said distal end of said twisting shaft is thereafter positioned in said second smaller diameter region of said support tube, said twisting shaft can sever that pair of suture ends.

5. A suture tensioner according to claim 4 wherein said support tube is formed with a crown configuration on its distal end.

6. A suturing system comprising:

a suture introducer comprising:

an elongated housing having a proximal end and a distal end, a first channel extending distally through said housing, and second and third channels communicating with said first channel and opening on the exterior of said housing;

said first channel being sized to receive the midsection of a loop of suture, and said second and third channels each being sized to receive a free end of the same loop of suture, and said second and third channels being configured so that when the midsection of a loop of suture is positioned in said first channel and one free end of the same loop of suture is positioned in each of the second and third channels, and said housing is positioned in tissue, pushing distally on the midsection of the loop of suture will cause the two free ends of the same loop of suture to exit the second and third channels so as to penetrate the tissue;

said elongated housing being hinged so as to selectively release the midsection of the loop of suture; and a suture tensioner comprising:

a support tube having a proximal end and a distal end, said support tube having a first larger diameter at its proximal end, a second smaller diameter at its distal end, and a transition section therebetween; and a twisting shaft having a proximal end and a distal end, said twisting shaft comprising a pair of elements pivotally connected together at their proximal ends;

said twisting shaft being configured so that (i) when said distal end of said twisting shaft is positioned in said first larger diameter region of said support tube, said twisting shaft can slidably receive a pair of suture ends, (ii) when said distal end of said twisting shaft is thereafter positioned in said transition section of said support tube, said twisting shaft can grip that pair of suture ends, and (iii) when said distal end of said twisting shaft is thereafter positioned in said second smaller diameter region of said support tube, said twisting shaft can sever that pair of suture ends.

7. A method for closing an opening in tissue with a length of suture, comprising:

placing the length of suture in a substantially U-shaped configuration;

passing the two free ends of the suture distally through the opening, so that the two free ends lie on the distal side of the opening and the bridge of the suture lies on the proximal side of the opening;

driving the bridge of the suture distally so that (i) the two free ends of the suture pass through the tissue so that they lie on the proximal side of the opening, and (ii) the bridge of the suture passes through the opening and lies on the distal side of the opening;

pulling the two free ends of the suture proximally so as to close the opening in the suture; and making the two free ends of the suture fast so as to hold the tissue closed.

* * * * *